United States Patent [19]

Wernikoff

[11] Patent Number: 5,489,782
[45] Date of Patent: Feb. 6, 1996

[54] METHOD AND APPARATUS FOR QUANTUM-LIMITED DATA ACQUISITION

[75] Inventor: Robert E. Wernikoff, Newton, Mass.

[73] Assignee: Imaging Laboratory, Inc., Newton, Mass.

[21] Appl. No.: 217,423

[22] Filed: Mar. 24, 1994

[51] Int. Cl.$^6$ ..................................................... G01T 1/20
[52] U.S. Cl. ................. 250/369; 250/363.02; 250/370.1; 250/371
[58] Field of Search ......................... 250/363.02, 370.08, 250/370.09, 370.1, 370.11, 371, 375, 395, 363.03, 363.04, 369; 364/413.24

[56] References Cited

U.S. PATENT DOCUMENTS

| | | | |
|---|---|---|---|
| 4,860,205 | 8/1989 | Jatteau | 364/413.24 |
| 5,107,122 | 4/1992 | Barkan et al. | 250/370.01 |
| 5,293,044 | 3/1994 | Klingenbeck-Regn et al. | 250/369 |

OTHER PUBLICATIONS

Robinson, D. R. T., "Maximum Entrophy With Poisson Statistics", in Maximum Entrophy and Bayesian Methods, 337–341, 1991.

King et al., "Fast Count–Dependent Digital Filtering of Nuclear Medicine Images: Concise Communication", Journal of Nuclear Medicine, 24:1039–1045, 1983.

Pratt, William K., "Image Sampling and Reconstruction", Ch. 4 of Digital Image Processing, 93–121, 1991.

Rollo et al., "Factors Affecting Image Formation", Ch. 10 of Nuclear Medicine Physics, Instrumentation, and Agents, 387–435, 1977.

Primary Examiner—David P. Porta
Assistant Examiner—David Vernon Bruce
Attorney, Agent, or Firm—Fish & Richardson

[57] ABSTRACT

The invention relates to forming an image from a random particle flux. Particles of the flux are detected by a discrete-cell detector having a cell size finer than conventionally used. Preferably, the cell size is sufficiently small that almost all cells of the detector count at most one particle during the image acquisition time. The count data are filtered through a band-limiting filter whose bandwidth lies between a bandwidth corresponding to the detector cell size and the flux bandwidth of interest. Outliers may be flattened before filtering. Neighborhoods around each cell are evaluated to differentiate stationary regions (where neighboring data are relatively similar) from edge regions (where neighboring data are relatively dissimilar). In stationary regions, a revised estimate for a cell is computed as an average over a relatively large neighborhood around the cell. In edge regions, a revised estimate is computed as an average over a relatively small neighborhood. For cells lying in an edge region but near a stationary/edge boundary, a revised estimate is computed by extrapolating from data in the nearby stationary region.

45 Claims, 10 Drawing Sheets

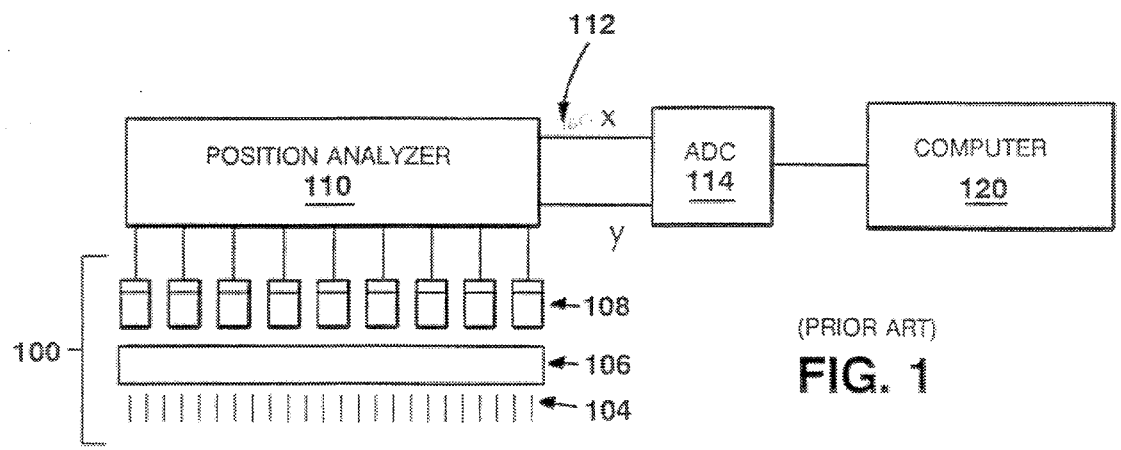
FIG. 1 (PRIOR ART)
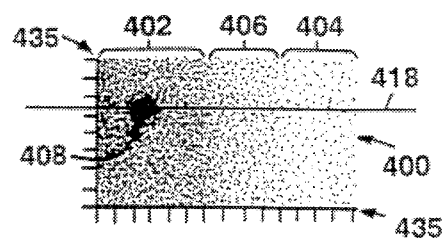
FIG. 4a
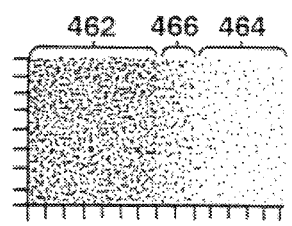
FIG. 4d
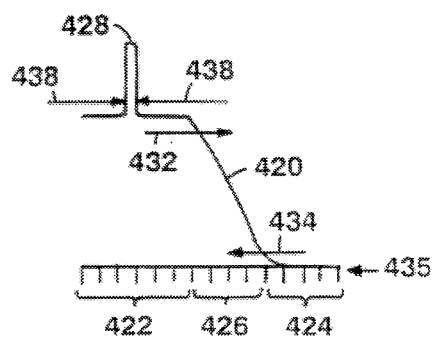
FIG. 4b
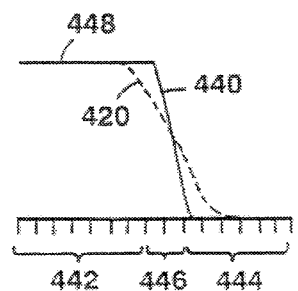
FIG. 4c

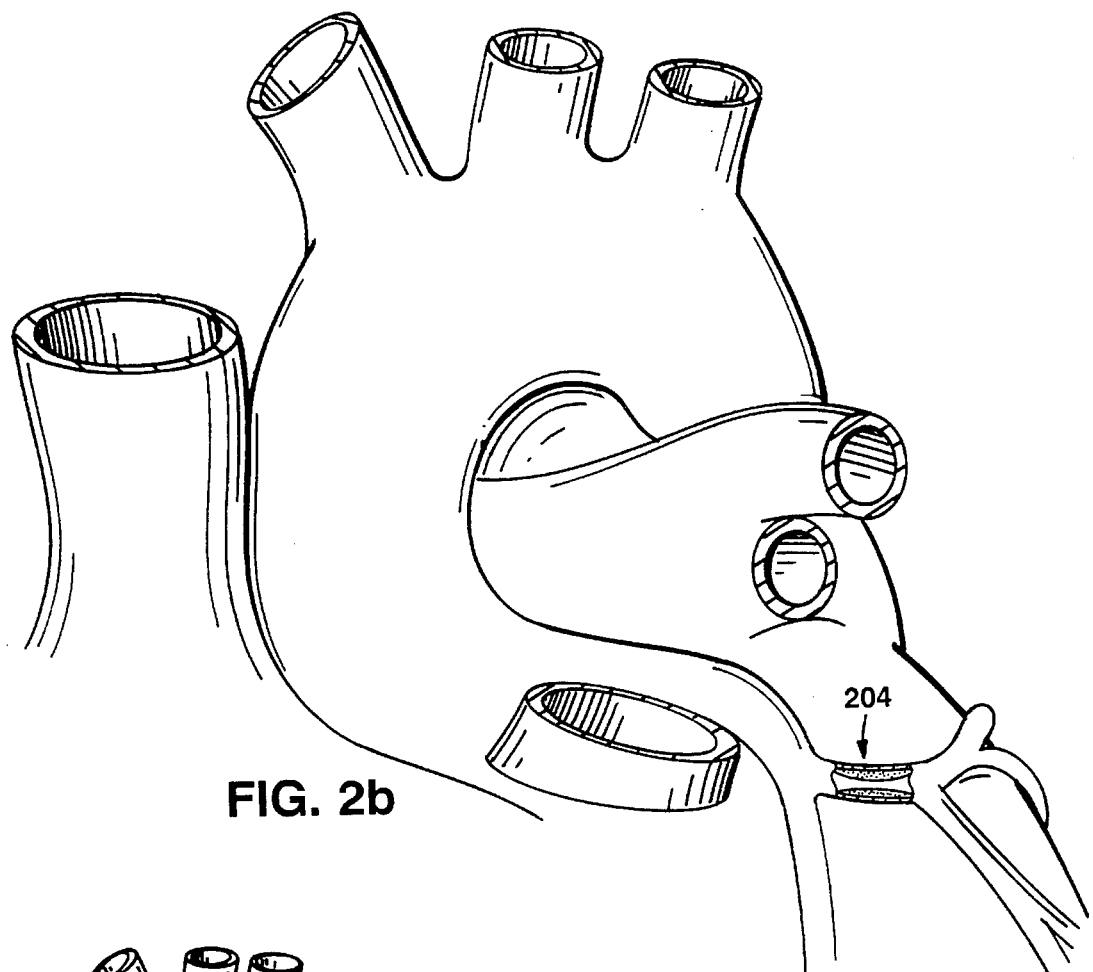
FIG. 2b
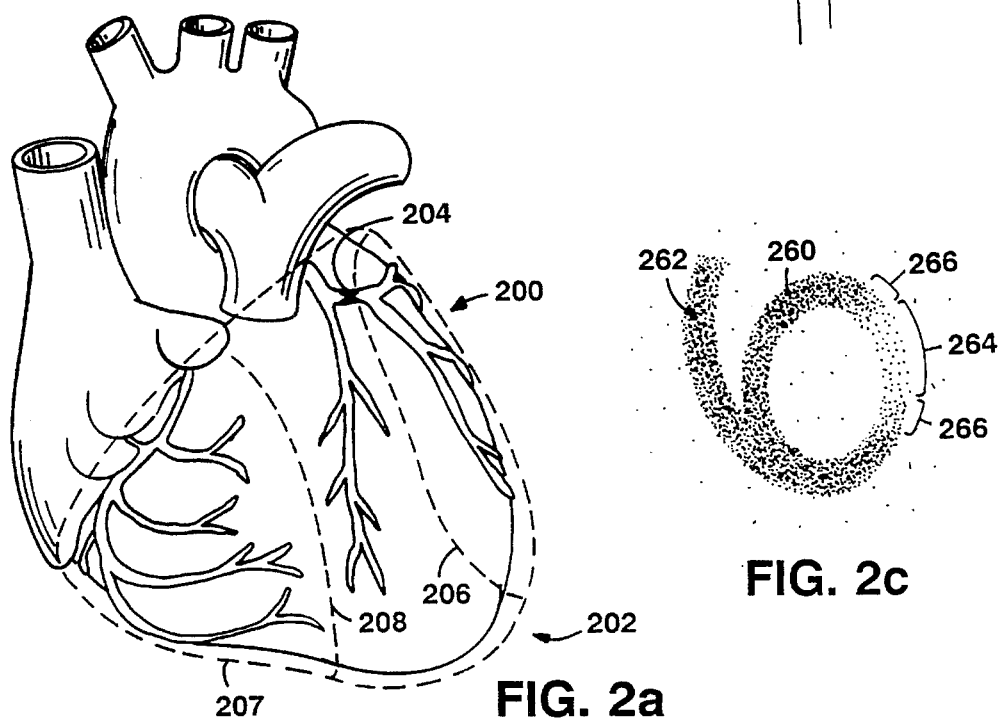
FIG. 2c
FIG. 2a

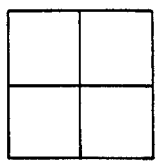
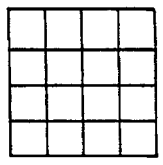
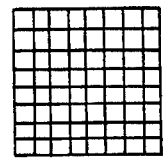
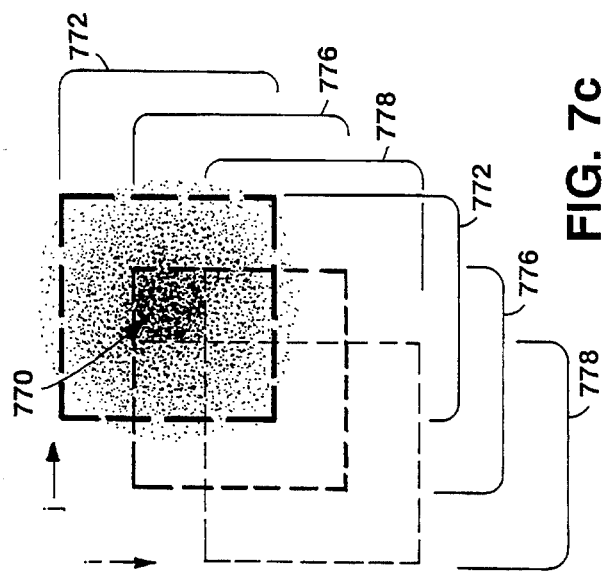
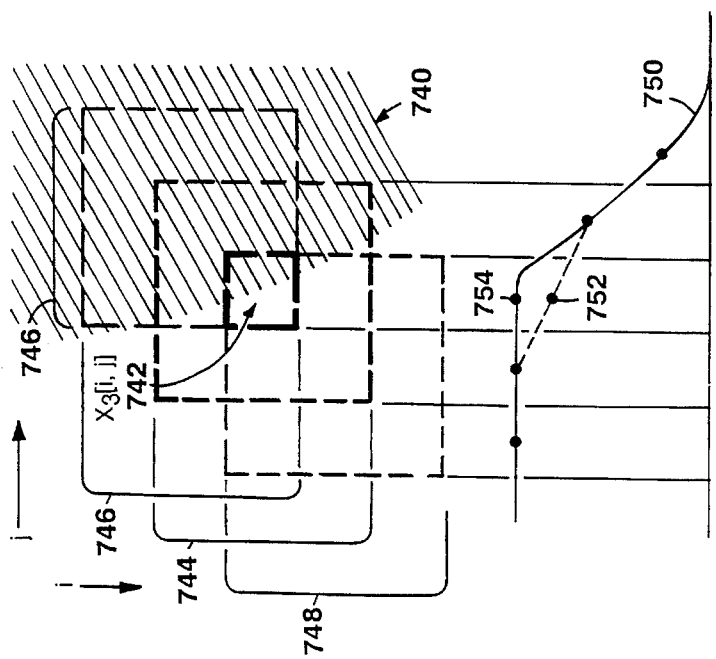
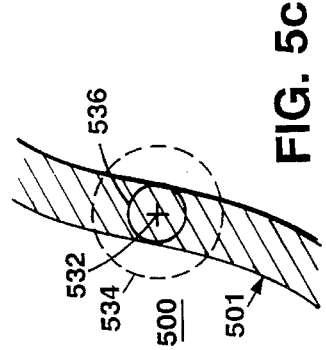
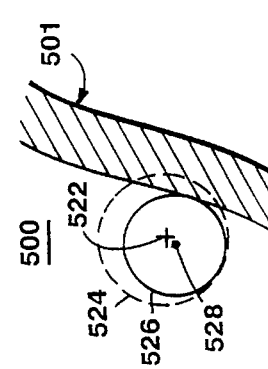
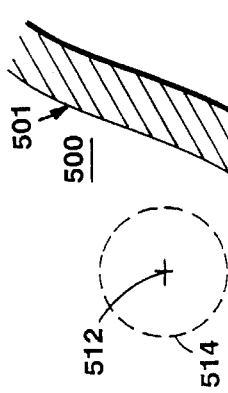

Incoming raw image values are $X_0[i,j]$

% 610: Compute a count-density function by passing the
% raw image through a two-dimensional, cylindrically-
% symmetric Butterworth filter of bandwidth 30.
$X_1$ = cylindrical_butterworth( $X_0$, 30 )

% 620: Reduce image noise by flattening outliers.
% 622: Compute the mean and standard deviation for the
% pixels in a neighborhood around each pixel
at each pixel [i,j] of the Butterworth'ed image $X_1$ do:
{
    select the pixels in a neighborhood around pixel
        $X_1[i,j]$ (for instance, the eight pixels in the 3×3
        cell around $X_1[i,j]$, or the edge pixels of the 7×7
        square [ i-3:i+3, j-3:j+3 ] around $X_1[i,j]$
    {
        calculate the mean mu[i,j] and variance sigma[i,j]
            of the neighborhood pixels
    }
}

% 624: flatten any outlier outside mu[i,j] ± K*sigma[i,j]
at each pixel [i,j] of the image do:
{
    if pixel $X_1[i,j]$ > mu[i,j] + K* sigma[i,j], then
        $X_2[i,j]$ := mu[i,j] + K * sigma[i,j]
    else if pixel $X_1[i,j]$ < mu[i,j] + K* sigma[i,j], then
        $X_2[i,j]$ := mu[i,j] - K * sigma[i,j]
    else
        $X_2[i,j]$ := $X_1[i,j]$;
}

% 630: Filter using a Butterworth filter of bandwidth 20
% to form a revised count-density function $X_3$
$X_3$ = cylindrical_butterworth( $X_2$, 20 )

FIG. 6a-1

```
% 640:  examine the neighborhoods around each point of X_3
% to determine whether the point is part of a stationary set
% vs. being an edge point.  (Example neighborhood: 3x3 array
% centered on the pixel).
% 642:  Find the mean mu and variance v of the points
% in each pixel's neighborhood
at each pixel [i,j] of the image do:
{
     select the pixels in a neighborhood around pixel X[i,j]
     {
          compute the mean mu[i,j] and variance v[i,j] of
               the X_3's in the neighborhood.
     }
}

% 644:  Find the largest of these variances.  Set a
% threshold value, for instance 0.03 times the largest
% variance.  Assume that any point whose variance v[i,j]
% exceeds this threshold is in an "edge" region, and all
% other pixels are in "stationary" regions.  Set array
% "is_an_edge" to 1 for edge points, 0 for stationary
% points.
varmax := max( v );
threshold := (0.03 * varmax);
at each pixel [i,j] of the image do:
     is_an_edge[i,j] = v[i,j] > threshold;

% alternate method for Step 644:
%   is_an_edge[i,j] = mu[i,j]/v[i,j] < 0.5

% 648:  At this point, "is_an_edge" looks like a line
% drawing of the scene, with 1's at edge points (areas of
% rapid change of the original grey-scale image X_0) and
% zeros in stationary regions.
```

FIG. 6a-2

% 650: In stationary regions, replace the original pixel
% values by their "local average values", and in edge
% regions by values computed in later steps. The "local
% average value" is obtained as a weighted average of the
% values of neighborhood points, using as the weighting
% function the impulse response of the 2-dimensional
% cylindrically-symmetric Butterworth filter of bandwidth
% 13.5. Since the majority of the final image points
% are to be replaced with such "local average values," we'll
% just compute it here once and for all.

652: local_average := cylindrical_butterworth( $X_2$, 13.5 )

at each pixel [i,j] of the image do:
{

654:     if NOT is_an_edge[i,j] then
656:         $X_4$[i,j] = local_average[ i, j ];

% 660: point [i,j] is not part of a stationary set.
% The general principle here is to look around the
% neighborhood of pixel [i,j] to see where there are
% stationary regions and where there are edge regions.
% If we find a nearby stationary region, compute a
% value for the local pixel as a function of the pixels
% in the nearby stationary region. In this embodiment,
% pick off eight vectors d of the points around point
% [i,j], for instance of length 3:
%  d[3,8]             d[3,1]                 d[3,2]
%       d[2,8]       d[2,1]      d[2,2]
%            d[1,8] d[1,1] d[1,2]
% d[3,7] d[2,7] d[1,7] X[i,j] d[1,3] d[2,3] d[3,3]
%            d[1,6] d[1,5] d[1,4]
%       d[2,6]       d[2,5]      d[2,4]
% d[3,6]             d[3,5]                 d[3,4]

662:     else if all eight directions have an is_an_edge pt
        within distance 3 then
    {
664:         $X_4$[i,j] := mean( $X_3$[ i-1:i+1, j-1:j+1 ] );
    } else {
666:         from the directions that have no edge points in
           "is_an_edge", pick the direction where the
           variance among the three points of
           "local_average" in the direction is a minimum
668:         $X_4$[i,j] := extrapolate from linear fit on three
           points of "local_average" in the picked
           direction
    }
} output image is $X_4$

FIG. 6a-3

% 700:  alternate method for determining edge regions vs.
% stationary sets, and extrapolating from stationary sets
% into edge regions.

702: Select parameters $\alpha_0$ and $\alpha_t$

704: Produce $X_3$ array with flattened outliers, for instance using
    method of step 620 of Fig. 6a 710: at each pixel $X_3[i,j]$ of the image do:
    compute the mean mu[i,j] and variance v[i,j] of the
        $X_3$'s in a neighborhood surrounding pixel $X_3[i,j]$ 712: From the neighborhood means mu[i,j] and variances v[i,j],
    compute $\alpha[i,j]$ at each pixel:
        $\alpha[i,j]$ = (N-3)/N * mu[i,j]/v[i,j]
    where N is the number of pixels in the neighborhood.

at each pixel [i,j] of the image do:
{
720:        compare to $\alpha_t$ the $\alpha$'s in the neighborhood corresponding
                to a 3×3 array of display pixels around and
                including $\alpha[i,j]$
722:        if all neighborhood $\alpha$'s are above $\alpha_t$   {
                % pixel $X_3[i,j]$ is in a stationary region.
                % Because $\alpha$ is high, the computed $X_4$ will use
                % relatively much information from its neighbors
724:            $X_4[i,j]$ = $\alpha[i,j]$*mu[i,j] + (1-$\alpha[i,j]$)* $X_3[i,j]$;
            }
726:        if all neighborhood $\alpha$s's are below $\alpha_t$   {
                % pixel $X_3[i,j]$ is in a transition region.
                % Because $\alpha$ is low, the computed $X_4$ will use
                % relatively little information from its neighbors
728:            $X_4[i,j]$ = $\alpha_0$*mu[i,j] + (1-$\alpha_0$)* $X_3[i,j]$;
            }
730:        otherwise, if they are mixed {
732:            among the [i,j]'s in the neighborhood, select $i_0$
                    and $j_0$ whose $\alpha[i_0,j_0]$ > $\alpha_t$ and mu[$i_0,j_0$] is
                    closest to $X_3[i,j]$
734:            $X_4[i,j]$ =
                    $\alpha[i_0,j_0]$*mu[$i_0,j_0$] + (1-$\alpha[i_0,j_0]$)* $X_3[i,j]$;
            }
}

FIG. 7a

METHOD AND APPARATUS FOR QUANTUM-LIMITED DATA ACQUISITION

REFERENCE TO MICROFICHE APPENDIX

A source code listing of an embodiment of the invention is attached as Appendix A, incorporated herein by reference.

Also incorporated by reference is Appendix B.

A portion of the disclosure of this patent document contains material that is subject to copyright protection. The copyright owner has no objection to the facsimile reproduction by anyone of the patent document or the patent disclosure as it appears in the Patent and Trademark Office file or records, but otherwise reserves all copyright rights whatsoever.

BACKGROUND OF THE INVENTION

The invention relates to construction of detectors of information-carrying fluxes of discrete particles, to the proper measurement and use of parameters measured from such fluxes, to forming perceptible images from data captured by spatially-discrete particle detector devices, and to removing aliasing from improperly sampled data.

It is known to measure a flux of particles using an array of detectors, for instance a CCD (charge-coupled device) array. The count from each element of the array can be used to determine a grey level for a pixel of a grey-scale image.

SUMMARY OF THE INVENTION

By employing the methods described herein, a reduced intensity of particle flux can be used to obtain images of higher quality and readability, lower noise, and better contrast, edge definition, and freedom from aliasing typically associated with higher flux values.

In general, in a first aspect, the invention features a method for forming a representation of a flux of discrete particles emitted by a plurality of random emitters of particles. The emitted flux has a random noise variation and an information-carrying variation having a bandwidth of interest. In the method, particles of the flux are detected by a detector that produces a quantized representation of each detection. The quantized representation is determined by a quantization cell size that is smaller than a cell size sufficiently small to preserve contrast for the smallest feature of interest of the information-carrying variation of the particle flux. The quantized representation data are filtered through a band-limiting filter of bandwidth less than a bandwidth corresponding to the quantization cell size but greater than the bandwidth of interest.

Preferred embodiments may include the following features. Each dimension of the quantization cell size is chosen be at most half the corresponding dimension of a detector cell size corresponding to Nyquist sampling of the bandwidth of interest. More preferably, the quantization cell size is sufficiently small that essentially all of the quantization cells each detect at most one particle of the particle flux. The band-limiting filter has a substantially non-negative and non-oscillatory response, and the filtered representation data approximate a continuous particle flux density function over unit areas of the particle detector, such that an integral of the particle flux density function over any set of cells of the quantized representation is approximately equal to the total number of particles detected in the cells of the set. The filter is cylindrically-symmetric. Before the filtered representation data is displayed as a visible image, random numbers are added to at least a portion of the data, a standard deviation of the random number added to each datum being related to an uncertainty in the value of the datum. Data acquired in cells of a detector with a relatively large quantization cell size can be randomly redistributed among smaller cells that subdivide the larger cells.

In second and third aspects, the invention features methods of processing a numerical image of data acquired by a location-quantizing detector, the data each having a first value and a quantized location. The method includes the steps of evaluating neighborhoods of the data, and alternative steps for determining estimated values. The evaluating step selects a neighborhood around each datum and evaluates the first values of the data in each neighborhood to differentiate stationary regions and edge regions of the data, the stationary regions being regions of the data in which the first values of neighboring data are relatively similar, the edge regions being regions of the data in which the first values of neighboring data are relatively dissimilar. In a first alternative step, applied in stationary regions, an estimated value is computed as an average of the first values over a relatively large neighborhood of data neighboring each stationary region pixel. In a second alternative step, applied in edge regions, an estimated value is computed as an average of the first values over a relatively small neighborhood around the edge region pixel. In a third alternative step, applied at pixels lying in an edge region but near a boundary with a stationary region, an estimated value is computed by extrapolating from values of data in the nearby stationary region.

Preferred embodiments may include the following features. The step of differentiating the stationary regions and edge regions has the substeps of: determining the variability of values of the first data in a neighborhood around each datum; comparing the neighborhood variabilities to a first threshold value; for a second neighborhood around each pixel, counting the number of neighborhoods within the second neighborhood whose neighborhood variabilities exceed the threshold; if the neighborhood count exceeds a second threshold, assigning the datum to a stationary region; and if the neighborhood count is less than a third threshold, assigning the datum to an edge region. The relatively low and relatively high variability conditions are determined at each datum by the steps of: determining the ratio of the mean of the first values in the neighborhood to a variance of the first values in the neighborhood; and comparing the ratio to a threshold value. Outliers may be flattened out for the data before the evaluating and differentiating step. For quantized vector locations within the edge regions and lying near two or more of the stationary regions, an estimated value is computed by choosing a preferred one of the near stationary regions, and extrapolating from values of data in the preferred stationary region. The evaluating and differentiating step further includes the step of producing a state map array of entries corresponding to the data of the image, each entry of the map indicating whether the corresponding image datum is in a stationary region or an edge region.

In a fourth aspect, the invention features a method for deconvolution filtering for processing a numerical image of data acquired by a location-quantizing detector. The data each have a first value and a quantized location. The method includes evaluating and alternative filtering steps. The first values of data in a neighborhood around each datum are evaluated to differentiate stationary regions and edge regions of the data. For each datum not near a boundary between a stationary region and an edge region, the method filters using an integration area centered on the datum and with a radius not exceeding the distance to the boundary. For each datum near a stationary/edge boundary, the method filters using an integration area asymmetric about the datum.

In a fifth aspect, the invention features a method of producing a perceptible image of an object on a display device, having the steps of: acquiring average and uncertainty color values corresponding to each pixel of a portion of the image, the average value estimating a value of a property in the corresponding region of the object and the uncertainty value estimating an uncertainty in the average value; and adding a random number to the average value for each pixel of the image portion, a standard deviation of each random number being related to the uncertainty value for the pixel; and displaying the randomized pixel values on the display device.

Preferred embodiments may include the following features. The method may further include the steps of: acquiring raw data from a transducer that samples a physical phenomenon; and performing a noise-reducing image processing step on the raw data to produce the average and uncertainty values before the adding step. The method further includes the step of selecting the image portion by randomly selecting a proportion of the pixels of the image. The method further includes the step of selecting the image portion by deterministically selecting a uniformly-distributed set of the pixels of the image.

In a sixth aspect, the invention features a method for improving the images produced by a device for forming an image from data collected by a particle detector, including the steps of: replacing the particle detector with a particle detector having a quantization cell size that is smaller than a contrast cell size sufficiently small to preserve contrast for the smallest feature of interest of the information-carrying variation in the particle flux; and adding to the image device a filter for band-limiting the quantized representation data, the filter having a bandwidth less than a bandwidth corresponding to the quantization cell size but greater than the bandwidth of interest.

In a seventh aspect, the invention features a method for forming a continuous representation of a discrete process, including the steps of: detecting events of the discrete process with a detector cell size sufficiently small that almost all cells of the detector count at most one the event; constructing from the samples a count density function; and estimating from the count density function an ensemble average count density function.

In an eighth aspect, the invention features a method for reducing aliasing noise in sampled data, including the steps of: sampling a phenomenon in a detector with a relatively large quantization cell size to produce a value for each cell of the detector; defining an array of cells, each detector cell corresponding to a contiguous group of cells of the defined array; and randomly partitioning the value of each detector cell among corresponding cells of the defined array.

Preferred embodiments may include the following features. The redistributing step includes the substep of assigning redistribution probabilities to each of the array cells, the redistribution probabilities corresponding to a smooth curve fit to data counts in each of the large cells.

When used in medical imaging, the invention can provide one or more of the following advantages. The patient can receive a lower dose of radiation. Undesirable portions of a particle flux signal can be ignored by using, for example, better collimators or selected portions of the energy spectrum to create a better and more readable representation. The camera can be made more directionally- and energy-level-selective, thereby excluding scattered particles and further improving the image. Imaging time can be reduced, thereby improving patient comfort and reducing blurring due to patient movement. Particles can be more selectively acquired: for instance, the camera can be turned off when the patient moves or breathes, and the camera can count photons at an energy less subject to scattering, even if those less-scattered particles are less abundant.

The benefits of the invention are not limited to use in Nuclear Medicine or medical imaging; the invention can be used to improve data acquired from any device that detects discrete particles and assigns discrete detection times or positions to the detected particles. These devices include two-dimensional imaging devices such as night vision devices, television cameras, PET (positron emission tomography) and SPECT (single photon emission computed tomography) scanners, three-dimensional imaging devices, and devices that operate in the time dimension, for instance radiation detectors for monitoring nuclear reactions. When used with these other devices, the invention provides lower-noise images with fewer photons, for instance allowing a night vision camera to operate in lower light conditions.

BRIEF DESCRIPTIONS OF THE DRAWINGS

FIG. 1 is a side view of a patient under a gamma camera.

FIG. 2a is a front view of a human heart.

FIG. 2b is a detail view of a human heart, partially cut away.

FIG. 2c is a left anterior oblique view of a human heart.

FIGS. 3a, 3b and 3c show the pixels of imaging planes of cameras.

FIGS. 4a and 4d shows a detail of a counted-photon image.

FIGS. 4b and 4c plot image count density against space.

FIGS. 5a, 5b and 5c show application of an adaptive filter to pixels of an image.

FIGS. 6a-1, 6a-2, 6a-3 and 7a are pseudo-code descriptions of programs combining filtering and extrapolation from stationary sets.

Figure 6B:
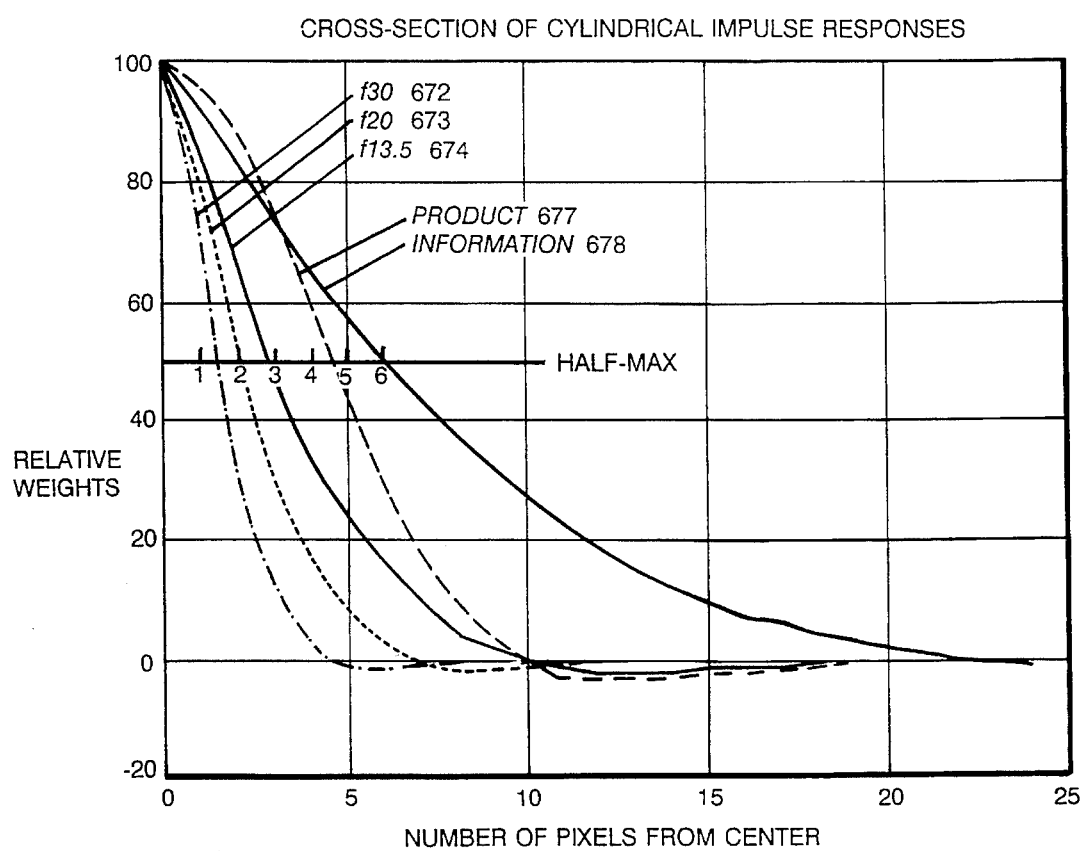

FIG. 6b shows cross-sections of impulse response of cylindrically symmetric filters.

FIGS. 7b and 7c show pixels of an image.

Figure 8:
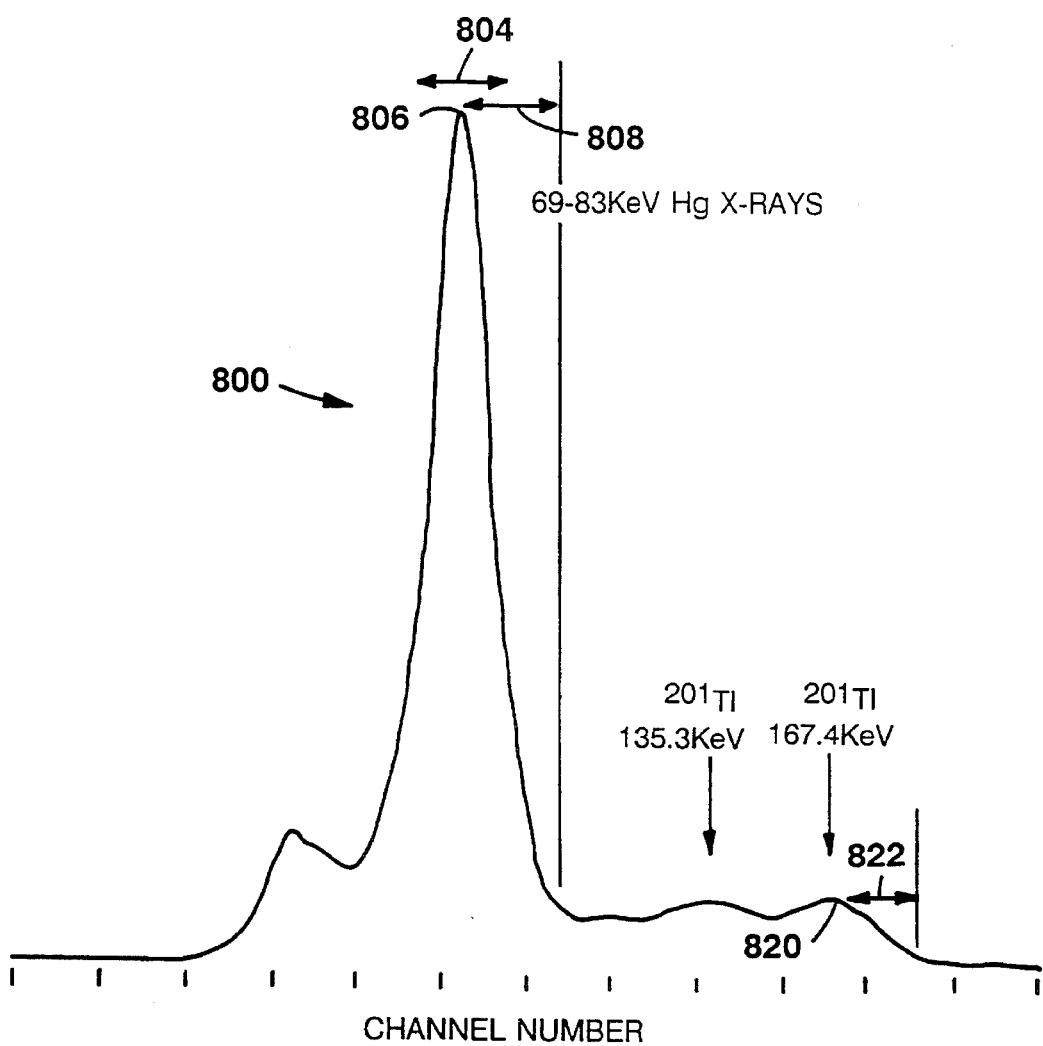

FIG. 8 shows a gamma spectrum of $^{201}$thallium.

FIGS. 9a, 9b, 9c and 9d show Nuclear Medicine images.

EXTENDED BACKGROUND

The invention is useful with detectors that detect discrete particles (photons, neutrons or other nuclear particles, or any other particles), provided only that the emitters of these particles operate at random, and the operation of any one emitter is totally unaffected by the operation of any other emitter in the source of the particle flux. Particular, though not exclusive, attention will be paid to the case in which the parameter measurements vary in space or time or both, thus providing the raw materials for the construction of, for example, static or moving images. For such static or moving images, the invention teaches the best way to assemble the parameter measurements into images.

The basic prior approach to detecting and measuring a particle flux is to subdivide space or time or both (depending on the problem) into cells and simply count how many particles arrive in each cell, but the way this is done in the current state of the art is wrong, as taught by this disclosure.

According to the prior art, in devising a detector array to measure the flux, there are two opposing considerations: on the one hand, to make the individual cells or bins of the detector somewhat smaller than the smallest feature of the flux that needs to be resolved with substantially no loss of contrast, and, on the other hand, to make the individual cells or bins as large as possible which, as will be shown, leads to a better signal-to-noise ratio. This reflects a basic necessity in any usable measurement system: the expected count must be large in comparison with the average amplitude of the fluctuations in that count. The latter is often measured by the standard deviation of the count, and the ratio of expected count to the standard deviation of the count—which could be called a signal-to-noise ratio, or SNR—efficiently summarizes the expected efficacy of the measurement system. To examine in more detail the tension between making cells as large and as small as possible, and how the pragmatic rules of thumb of the prior art resolve those tensions, consider the following simple example. Suppose that the purpose of some particular flux of particles is to form an image which is completely uniform except for a small spot of diameter not less than d and low contrast c somewhere in the image area, and suppose further that the object of this elementary imaging system is to determine if there is a spot, and where it is. (Contrast is defined as the fractional difference in the count-densities or brightnesses of two areas; for example, if the brightness in two adjacent areas is a and b, a>b, the contrast is c=(a−b)/a.) In devising an array of square detectors for the particle flux that contains this information, current thinking would be torn between wanting to make the cells in the array as large as possible, so as to maximize the SNR and thus make it more likely that the low contrast c will be seen among the surrounding fluctuations; and wanting to make the cells smaller than d on a side, because otherwise the spot area might often be shared among as many as four different detectors, and the small difference in count at the spot might thus be diluted in each detector with counts corresponding to the background, greatly reducing the contrast "seen" in each detector, and making the spot less visible. The current rule of thumb would be to make the detectors d/4 on each side, and thus ensure that at least one detector sees the spot at full contrast.

But it turns out, as is taught hereinbelow, that this prior art approach is wrong. The question of how best to assemble an image from a random flux of particles is not a trivial question, and its answer is not accessible by unaided common sense. And when the problem is solved properly, as is taught herein, the images have simultaneously greater contrast, much more resolution and less noise than any images assembled by the conventional unaided common sense that constitutes the present state of the art.

What is wrong with the conventional thinking of the prior art is that it overlooks, to its detriment, the fact that examining the particle flux with discrete detectors is the equivalent of performing spatial sampling of the spatial distribution represented by the particle flux, without first having band-limited that spatial distribution. And it is an elementary fact of the Nyquist-Shannon Sampling Theory, well known to those versed in the art, that sampling of a signal, without first bandlimiting, results in aliasing—that is, the importation of noise from remote areas of the frequency spectrum into the frequency band, defined by the reciprocal of twice the sampling spacing, where the desired signal resides, and from which, according to conventional received wisdom, the aliased power can never again be removed. As this point is basic to understanding the invention, it deserves further discussion.

Consider a basic distinction between, on the one hand, a canonical situation in which there is an analog source of signal—for example, a sensor that measures temperature or light intensity—whose output voltage is first bandlimited by an analog filter and then sampled in accordance with Nyquist-Shannon Sampling Theory; and, on the other hand, the situation prevailing in most modern image detectors, in which the sensor's image plane is, by construction natively subdivided into cells, which corresponds to performing spatial sampling of a spatial signal that in fact was never available in analog form, and hence never could be properly band-limited by an analog filter before the sampling occurred.

This problem is not inherent in the use of particle fluxes. Mostly, it is a consequence of the use of solid-state devices as particle detectors, such as CCD's and the like. In the past, when TV cameras were vidicons, the optical system formed a continuous distribution of charges on a photoconductive target, and an electron beam swept smoothly past the charges and, in effect, "read" them. The output was a continuous signal (at least, in the "x" dimension) which could have been band-limited using an analog filter and then properly sampled. It is known from Sampling Theory that a heavy penalty is incurred if signals that are not band-limited are sampled, and it is clear that, no matter how defocused (and hence smoothing) the optics of an imaging system may be, if the photon sensor counts individual photons, then the spatial signal into the sensor contains wide-band power, and it should not be sampled before suitable band-limiting. But there is no analog signal here to band-limit. That is the problem the present invention addresses and it is a very basic, general problem.

There is, of course, a basic question, namely, is the problem worth worrying about? If all the right things are done, even if only approximately, is enough improvement available to make it worth the trouble? It turns out that the potential for improvement is remarkable, as the following heuristic argument demonstrates.

Suppose that the particle flux that forms an image is regular instead of random; that is, suppose that the picture elements, or pixels, that form the image are like little bins in which counters are placed by a deterministic process that places in each bin precisely the correct number of counters to represent the gray level desired for that pixel. How many particles would one need to collect per pixel in order to distinguish nearby pixels whose contrast is, say, 5% (this is better that the contrast discrimination aimed for in many current medical devices)? To distinguish a contrast of five percent (that is, one level in twenty) only 20 possible levels in the darkest interesting portion of the image are needed. In some medical images, and also in many other fields, the difference between brightest and darkest levels in the interesting portions of the image might be of the order of 2:1. So if 40 levels (=40 particles/pixel) are available in the brightest area of the image, the required contrast discrimination would be achieved if the particles are deposited in an orderly, as opposed to a random, way.

How many particles are needed in the random case? To detect a contrast of five percent, the signal-to-noise ratio must be at least 20:1; indeed, it must be much greater. That is, if a level a is to be distinguished with some assurance from a level b, then the difference a−b must be large compared to the likely fluctuations in either a or b. Otherwise, a chance fluctuation in either level would frequently result in an error. According to the prior art, the required signal-to-noise ratio (SNR) is at least 60:1.

Most objects emit particles in a random way, for instance with each volume or surface element of the object emitting particles with random amounts of time between the particle emissions. Over a relatively short imaging time, some parts of the object will emit "too many" particles, and some "too few" (compared to the proportion of particles these parts would emit if the image could be formed over a much longer time). Most particle sources have Poisson statistics, for which an average count of n is associated with a standard deviation of $\sqrt{n}$. Thus the SNR equals $n/\sqrt{n}=\sqrt{n}$. For the SNR to be 60, n must equal 3600. Thus in the random case to achieve the same contrast detection requires ninety times as high a particle count as in the orderly case. This shows the exorbitant cost of randomness, and the opportunity for improvement that might be achieved if the particle flux could somehow be regularized (even if only approximately) and if introducing unnecessary distortion through maladroit sampling is avoided.

The preferred method and apparatus presented in this disclosure approximately regularizes photon flux; thus the invention achieves a level of performance somewhat comparable with orderly, as opposed to random, particle deposition. The saving in required counts/pixel can readily be converted into other desirable attributes, which are too many to list if one takes into account all the possible applications of this disclosure. The list below, therefore, will be limited to only one subset of the field of medical imaging, namely, Nuclear Medicine.

There are many examples of important improvements in Nuclear Medicine imaging practice which, though known and possible in a theoretical sense, are never actually used because each entails an unacceptable loss (one-half or more) of imaging photons, and in the current, rather marginal, state of the art, such a loss is regarded as intolerable. In operation according to the invention, however, these improvements become perfectly feasible in practice. The following is merely a sampling of several Nuclear Medicine applications.

1. Acquiring lung, liver and heart scans with respiratory gating, thus reducing the current false-negative rate in lesion detection. Since the end-expiration phase provides images free from the blurring effects of motion, and lasts for roughly half of the entire respiratory cycle, this benefit may be obtained by giving up roughly half the available photons. This, and other forms of physiological gating, provide a powerful way to improve the contrast and resolution of medical images uses the method and apparatus of the invention.

2. Acquiring $^{201}$thallium myocardial perfusion scans using the 167 KeV thallium photons. This procedure would greatly reduce the false-positive rate currently experienced, and which is caused by excessive soft-tissue absorption of the low energy 76–83 kev thallium photons used in the prior art. Switching to the higher energy photon requires giving up roughly ⅘ of the photons, which is still well within the range that the method and apparatus of the invention make possible.

3. Acquiring cardiac blood-pool studies by accepting only photons at the higher end of the photon energy spectrum, a procedure that largely excludes scattered photons. Scattered photons result in misleadingly low estimates of cardiac ejection fraction in all but very thin-chested patients. Since the ejection fraction is a powerful prognostic indicator in the management of heart patients, and its measurement is half the reason for doing blood pool studies, this is an important improvement, obtained despite the loss of about ½ of the otherwise used photons.

4. Acquiring images using higher resolution collimators. Low resolution is the main criticism of Nuclear Medicine methods. It is regretfully accepted because, for example, doubling camera resolution entails losing ¾ of the photons, which is not feasible in current practice. The method and apparatus of the invention make this higher resolution acceptable with realistic ranges of photon counts.

5. It is well-known that contrast is the main ingredient needed by the eye of the interpreter to derive information from images. It may easily be shown that contrast may be increased at will by raising the image values to a power greater than 1. This procedure cannot be used in a noisy image, because the resulting magnified noise would overwhelm the viewer. With the nearly noise-free images produced by the method and apparatus of the invention, this process is perfectly feasible.

These and other improvements, whose net effect is to change, for the better the entire practice of Nuclear Medicine, become feasible when images are acquired properly, as taught by this invention. Comparable improvements are feasible in other forms of medical imaging (PET, CAT and SPECT scanners, but not MRI or ultrasound scanners), and also in improving the resolution of CCD-based TV cameras and night-vision devices with no sacrifice in signal-to-noise ratio or acquisition speed.

Prior art methods of forming images proceed from the following formulation of the problem: Given raw data (which might be an image) D(i,j), find an operator $\Omega$ such that the result $R(i,j)=\Omega[D(i,j)]$ minimizes some measure of distance $\mu$ between R(i,j) and some ideal, which often is the undistorted information content of the flux, say I(i,j). For example, $\mu(R,I)$ might be the mean square difference, in which case the operator $\Omega$ would be said to minimize the error power.

The present invention, on the contrary, does not start from data D(i,j) collected by some existing arbitrary detector. Rather, the method and apparatus of the invention prescribe how to build an improved detector and then how to process the data it produces. Thus the operation of the invention cannot be put in the classical form of an operator working on existing data. There is no prior art operator that produces the result of the present invention starting from existing data. (It will be shown, however, how to obtain a rough approximation to the output of the present invention in those cases where, for some reason, it is not possible to obtain control over the machinery that acquires the data. This would be true, for example, if the data were archival, or if the particle detector cannot immediately be modified according to the present invention. It will be evident that the approximate result obtained in such cases can never be as good as what would be obtained if a particle detector constructed according to the invention were in use.)

What is wrong with prior art approach is that it begins with data that have much more noise and distortion in them than they would have had they been acquired in accordance with the invention. Thus, conventional workers start from a place that is much worse than it needs to be, and all their skill never undoes the initial disadvantage. They frequently also suffer from a more subtle problem, from which the approach according to the invention is free. Norbert Wiener, in his classic *Interpolation, Extrapolation, and Smoothing of Stationary Time Series,* M.I.T. Press and Wiley, New York, 1949, brought to the engineering world the concepts of a random process—a sequence of values generated by a mechanism whose productions are, to some extent, inherently unpredictable, but whose statistics (i.e., mean, variance, probability distribution, etc.) are unvarying.

Wiener postulated the notion of the set of all possible outputs of such a process, the set being called the ensemble and each member of the set being called a realization of the ensemble. The statistics of the process—for example, the mean, and other averages—are thought to be obtained by averaging over the members of the ensemble. In cases where the process is ergodic—that is, its statistics are unvarying in time (or space, depending on where the process is taking place) and every realization sooner or later assumes the character of every other realization, the averages calculated in time are equal to the same averages calculated over the ensemble. Having postulated this model, which in no way resembles circumstances prevailing in noisy images, Wiener then developed the idea of the optimum filter, this being an operator whose output minimizes the mean square difference between itself and the underlying noise-free signal. Working with a random process which he thought of as extending infinitely in both directions, the formulation of the optimum filter made sense. His many successors, however, are seduced by Wiener's elegance and apply the same thinking to finite images, which are non-stationary, and hence non-ergodic and these workers are satisfied if they derive an "optimum filter" which minimizes the ensemble average mean square error. But they should not be satisfied, because in a non-ergodic case there is no connection between the ensemble average, and what the filter does to any one realization of the process—for example, one acquired by a particular particle detector on a particular day. On that particular realization, the filter's operation might actually give quite mediocre results. Great improvements result when, as described in connection with this invention, ideas of optimum filters are abandoned as inappropriate, and statistical estimation is used instead, in conjunction with properly constructed detectors.

Extended Overview of the Invention

The key realization underlying this invention is that the individual detectors of a detector array used to measure a particle flux should be built very small and positioned very closely together. Ideally, they should be so small, that within the acquisition time, they are very unlikely to acquire more than one particle. This criterion is very different from the prior art understanding, where detector sizes were determined as some fraction of the size of the smallest feature that needed to be detected without loss of contrast. To prefer the (0,1) case—that is, the ideal case in which the vast majority of detectors of the detector array detect either no particles (0) or at most one (1)—is profoundly counter-intuitive because, as was shown earlier, the signal-to-noise ratio in any image formed directly from the counts detected in each cell location increases as the count per cell increases. This provides the major motivation in prior art conventional practice for making each cell as large as possible. And, indeed, if an "image" were made by mapping the counts detected by each detector in the (0,1) case—or even in a modestly low-count case that merely approximates the (0,1) case—the "image" would be totally illegible, which by itself is a major step backward from current practice. But if these illegible data sets, the raw "images", are assembled properly into images using the methods described hereinafter, the result is much better than any conventionally produced image, and even better than the result of any operation that could be applied to prior art, conventionally-acquired, data.

This can be understood better from the physics of the postulated information-carrying particle flux. The flux is produced by emitters whose operation is in no way affected by the emissions of any other emitter in the source of the particle flux. More concretely, consider specifically an image in two or more dimensions. For the imaging devices to be described, it can be shown that random fluctuations in particle count in any one detector of the array are statistically independent of fluctuations in any other detector, no matter how small or how close the pair of detectors may be, and that the sum of the variances of the particle count over all the detectors spanning a given space is constant, whatever be the size of the detectors. ("Statistical independence" means that it is impossible to predict the size of a fluctuation in one detector from knowing the size of the fluctuation in another. An example of two processes that are statistically independent is tossing two dice: knowing what value turned up on one die provides no information to help predict what will turn up on the other. "Statistical independence" need not imply that the two processes behave remarkably differently—for instance, even though both dice will likely turn up a six about ⅙ of the time, they are still statistically independent. Nor need statistical independence imply independence from external factors: two dice loaded the same way so that six comes up ¾ of the time are still statistically independent.) What follows from this result is new and remarkable.

Suppose that the detector array was originally constructed to sample the particle flux at the spacing appropriate to the bandwidth of the information carried by the flux. Consider what happens if the detectors are made smaller, so that the sampling of the flux occurs with a smaller spacing. The noise power, which was originally distributed uniformly over the set of frequencies in Fourier space occupied by the signal, will now be spread uniformly over the larger set of frequencies corresponding to the closer spacing of samples. At the same time, however, the closer spacing does not change the set of frequencies occupied by the information. But since the total noise power (the sum of variances) available for spreading out over the larger frequency set has not increased, it follows that the noise power left within the signal band must have decreased. Since any power outside the information set of frequencies may be eliminated without damaging the information, it follows that one may ultimately recover the information with much less noise than it had when the flux was originally sampled at the prior art rate, supposedly "appropriate" to the information.

The process of eliminating power outside the signal set of frequencies sounds as if it could be done with an ordinary, suitably-adjusted, low-pass filter and, indeed, such a filter (a member of a novel class of very efficient filters, called cylindrically-symmetric Butterworth filters) has been used on data from an oversampled particle flux. The information signal obtained is much better than what is accepted in the current state of the art. However, a second feature of the invention and which is an integral part of the invention, follows from the fact that an ordinary linear filter is not the best procedure. The invention provides a large family of other non-linear processes, any of which is better (some much better) than any linear filter. The reason for this is fundamental, and is related to the lack of relevance of N. Wiener's work to images. Statements such as "for pairwise independent samples, noise power is uniformly distributed in frequency" which lead to classical solutions like, for example, linear filters with Wiener choices of parameters, are really statements about ensembles of noise rather than about the particular member of the ensemble with which one is confronted on any given day. The optimum linear filter minimizes the average value of some error criterion over the entire ensemble; thus it produces a solution which may be good on the average but, in fact, is often a mediocre choice for the particular member of the ensemble before us on any given day. A practical manifestation of this is that any given realization of the ensemble has frequent outliers (i.e., values that are atypically high or low, as one would expect in any random process) and these outliers act as a random distribution of delta functions of various sizes which, upon linear filtering, become the centers of varyingly-visible copies of the impulse response of the filter. These copies, whose size and distribution are specific to the realization rather than to the ensemble, are superimposed on the information. If, for example, the information is an image, the spurious impulse responses have the appearance of random blobs of low-frequency noise so that it is not true that the signal is recovered unharmed, as a superficial reading of the theory would have us believe.

Thus the general approach to the separation of information from noise taught by this invention is statistical estimation rather than pure linear filtering, and the hallmark of it is the insertion of a statistical estimation stage (usually non-linear) ahead of, after, or even in place of, the linear filtering stage. This estimation stage uses all available prior information about the image-forming system and about the imaging protocol, as well as the measured data, to arrive at the best posterior estimate of the ideal image (the nature of the ideal image is by no means obvious, and is further discussed below). To understand intuitively how prior information can be effective in estimation (that is, in constructing good images from bad data) note, for example, that detailed information about the pulse-spread function of a camera puts a bound on how different two nearby values of an image can be, so that any difference greater than that bound must be attributed to noise rather than to reality, and can largely be eliminated. This kind of consideration is described below.

As explained earlier, the specification of the detector assembly is an integral part of the invention; however, in some important practical cases the detector and acquisition process cannot be controlled. This is the case, for example, if it is required to re-examine old data from files, or if there is no choice about continuing to use existing, expensive equipment that cannot easily be retrofitted with a new detector assembly. Thus the invention features two good, but suboptimal, solutions which are described below for such cases. One solution departs from cells of conventional size, is very fast, but requires that the counts per cell in important areas of the image be no smaller than about 75. The other solution does not have this limitation, and depends on a random interpolation process to approximate the conditions obtaining with a large array of small detectors. The latter version of the invention is remarkable because it is quite effective in removing much of the aliased distortion introduced into an information signal by maladroit sampling. This result is particularly impressive considering the conventional wisdom that once aliasing distortion caused by improper sampling has corrupted a signal, it is impossible to remove it because the aliasing power occupies the same frequency band as the signal, hence cannot be separated from the signal.

It is useful now to consider what is the ideal image that the method and apparatus of the invention are trying to approximate. Prior art conventional imaging methods suffer from the fact that their so-called common-sense construction introduces some very hurtful distortions right at the start, which later cannot be undone (the aliasing discussed earlier). These distortions are avoided by starting at an irreducibly basic level. At this level, the proto-image (that is, the makings of a future image which, however, is not an image yet) is ideally a two-dimensional spray of unit event markers in continuous space. The markers mark the points where a particle arrived; clearly these are geometrical points, without extension or character. If the markers were thought of as points of light, for example, on the screen of a storage oscilloscope, those points of light, all with the same brightness, would not form a gray-scale image in our eyes unless the points were packed so closely together that the pulse-spread function of our eyes blended them into a "point-density per unit area" function. This suggests that an image is not the original collection of arrival points of particles, but rather a function describing the spatial density of arrival points.

The same conclusion can be reached by reasoning mathematically. An image composed of a finite number of particles contains all sorts of random features. The corresponding ideal image is obtained by considering the infinite ensemble of finite-particle images, and taking the average of the ensemble. But this ensemble average also does not converge to a gray-scale image (that is, an image having a continuum of brightness values) unless one has first constructed count-density functions out of the original markers of particle arrival for each of the members of the ensemble. Thus, without making arbitrary choices, we arrive at the concept that the ideal image being constructed is the ensemble average of count-density functions defined on the proto-images.

Finally, it should be noted that in a camera that uses a television or infrared charge-coupled device (CCD), and in medicine in the case of CAT and PET scanners, to practice this invention one must literally take a screw driver and soldering iron to the camera, and replace the detector assembly with a new assembly manufactured, according to the method and apparatus of the invention, with smaller detector cells and more of them. This is not so for gamma cameras, or for the SPECT cameras based on gamma cameras, widely used in Nuclear Medicine. In such cameras, as will be seen, the array of discrete detectors is actually composed of a single large detector crystal which is subdivided into discrete cells, not physically, but by the way data is organized in the memory of an associated computer. Thus these cameras lend themselves easily to experimentation with arrays of detectors of various sizes at substantially no cost, since changing the detector size amounts to a small software change in the associated computer. Thus gamma cameras are a convenient example to illustrate the invention, and for that reason a detailed description of a gamma camera is presented below. But it is important to realize that once the "detector assembly" has been defined and fixed for the gamma camera, the remainder of the description has full generality.

Figure 9A:
Figure 9B:
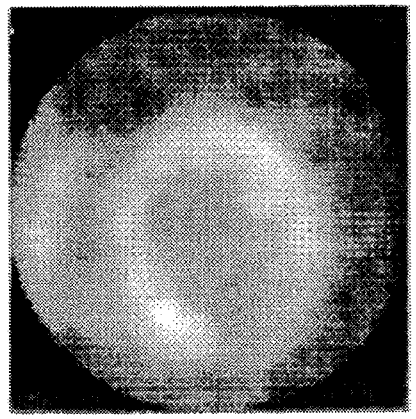
Figure 9C:
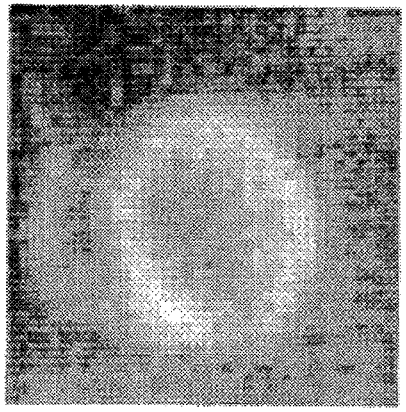
Figure 9D:
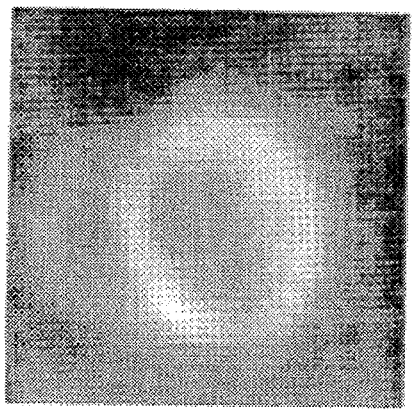

FIGS. 9a–9d each show a cross section of a living human heart whose muscle (myocardium) has been made radioactive by injecting the patient with $^{99m}$Technetium-isonitrile (Dupont-Pharma). The circular shape is the left-ventricular myocardium, and the flap to the left is a portion of the right-ventricular wall. FIG. 9a shows raw data acquired by an oversampling camera and displayed using conventional methods. FIG. 9b is an image of the data of FIG. 9a formed by the methods of the invention. FIG. 9c is an image acquired and displayed using methods conventional to Nuclear Medicine—that is, the raw data acquired by a conventional camera. FIG. 9d shows an image formed from conventionally-acquired data and processed by prior art image processing software.

FIG. 9b shows the benefit of using the bandlimiting and estimation stages taught by this invention, and higher-energy photons. The higher primary-to-scatter ratio of these photons expresses itself in much higher contrast between light and dark areas of the image. In FIG. 9b, a large lesion is immediately visible at the 5 o'clock position, indicative of partial occlusion of the coronary artery supplying that portion of the heart. This lesion is practically invisible in the conventional image of FIG. 9c. FIG. 9b also clearly shows the papillary muscles (the two finger-like structures projecting from the inner right-hand wall). These crucial muscles are completely blurred in the conventional image of FIG. 9c. Indeed, papillary muscles are almost never seen in the conventional practice of Nuclear Medicine; making them visible is one of the new contributions of the present invention.

Both sets of raw data, FIGS. 9a and 9c, were acquired simultaneously by a single gamma camera equipped with two independent energy analyzers and supplying data to two independent portions of computer memory. Thus any differences between the two images of FIGS. 9a and 9c due to camera positioning or differences in the state of the heart have been avoided. Both image acquisitions were also physiologically gated to the electrocardiogram. Each image is a snapshot of the period immediately following enddiastole, representing the first 50 ms after the onset of the EKG R-wave.

FIG. 9c was acquired with a conventional cell size. The energy analyzer window was set in the conventional way.

The data of FIG. 9a were acquired with the window set 10% above the 140 KeV photopeak of Technetium (thereby counting only 40% as many photons as the conventional image of FIG. 9c) with a cell ¼ as large as a conventional size cell in each dimension, or ¹⁄₁₆ as large in area. In combination these two factors yield, for each pixel of FIG. 9a, a signal-to-noise ratio ⅙ that of corresponding pixels of FIG. 9c. Accordingly, the oversampled image in FIG. 9a is virtually unreadable.

FIG. 9d is the result of noise-removal processing of FIG. 9c using the filter offered in the commercial software provided by Adac Corporation with their Nuclear Medicine computer, a standard piece of equipment used in perhaps half of all Nuclear Medicine laboratories. The smoothing properties of this filter effectively remove the noise, but they also remove all trace of the myocardial lesion, not to mention the papillary muscles.

Description of Preferred Embodiments

One example of a conventional spatially-discrete camera is shown in FIG. 1. In Nuclear Medicine imaging, a patient 102 is infused with a radionuclide gamma source (or other source of particles) that is taken up selectively by tissues of the body. The photons emitted by the radionuclide are spatially sorted and counted by the detector cells of a camera 100; the counts in the detector cells are used to determine color values of pixels in a displayed image. (As used herein, the word "camera" includes a very broad range of imaging devices, including "focusing" devices having collimators and/or lenses, and devices including spatially-discrete imaging surfaces such as those including arrays of CCD's (charge-coupled devices). Similarly, "color" may include true color, false color, grey scale, or half-tone black and white. Similarly, the particles may have been emitted by an object of interest or transmitted through it. The major components of gamma camera 100 are a collimator 104, a thallium-doped sodium iodide crystal 106, and an array of photomultiplier (PM) tubes 108. The outputs of PM tubes 108 are fed to a computer 120. Collimator 104 is typically a lead "honeycomb" of hexagonal openings, and passes only those photons whose trajectories are within a few degrees of parallel to the longitudinal axes of the openings—and then impinge on a thallium-doped sodium iodide crystal which scintillates as each photon passes through it, and PM tubes 108 detect and amplify this scintillation. Position analyzer 110 analyzes the responses from the multiple PM tubes 108 that respond to each photon, to determine the coordinates of the scintillation on the camera imaging aperture. The coordinates are expressed digitally in some cameras, or by analog values of waveforms in others. In the latter case, analog-to-digital converters 114 convert the coordinates to digital form and supply them to a computer 120. Computer 120, whose memory has been organized into cells—that is, ranges of coordinate values—that correspond to the desired spatial quantization of the camera's imaging surface, then increments by one the value stored in the cell corresponding to the area where the scintillation occurred. At the conclusion of acquisition, the counts in each cell can be used, for example, to assign a brightness value to pixels of a computer display monitor, thus forming a visible image corresponding to the received distribution of photons.

Referring to FIGS. 2a and 2b, gamma cameras are used in myocardial perfusion scans to evaluate patency of coronary arteries, that is, arteries that supply the heart 200, for instance to determine whether patient 102 should be catheterized. Patient 102 is placed on a treadmill or other exercise device, and at peak stress is injected with radioactive thallium. The thallium distributes in working muscles as does potassium, and hence should be distributed in proportion to muscle mass. But in fact, the thallium distributes in proportion to blood flow to various portions of the myocardium at moments of peak stress. Then, the patient is placed under gamma camera 100. One common orientation is the left anterior oblique (LAO) view, shown by arrow 202 in FIG. 2a. If the patient has, for example, an occlusion 204 of the left anterior descending branch of the left coronary artery, the region outlined by dotted line 206 will be partially ischemic, that is, receiving too little blood, and thus will have taken up relatively less thallium per unit volume than the parts of the myocardium served by non-occluded or non-ischemic vessels.

Referring to FIGS. 2a and 2c, the left ventricle (outlined with a dotted line 207) is essentially conical, and the right ventricle (outlined with a dotted line 208) is an overlying pouch. Thus, in an LAO view the left ventricle, outlined by dotted lines 207, images as a circle 260, and the right ventricle as a smaller adjoining pouch 262. Ischemic region 206 shows up as a deficiently radioactive region 264 (between transition regions 266) in the left ventricle 260.

Because radionuclides decay according to Poisson statistics, the standard deviation in the photon count of any cell of the gamma camera equals the square root of the number of counts. This deviation manifests itself as noise in the image, that is, pixels that are brighter or darker than they would be if a stable distribution of the radionuclide could be maintained and the image were accumulated over an infinite time. The signal-to-noise ratio (SNR) for a Poisson process is $n/\sqrt{n}=\sqrt{n}$, where n is the number of counts detected. From this, it follows that to increase the SNR of each cell, one needs to increase the average number of photons counted by each cell of the camera. This may be done by increasing the amount of time over which the image is accumulated, increasing the amount of the radionuclide injected into the patient, increasing the size of each pixel of the detector, setting the energy analyzer window of the detector at the photopeak of the gamma ray of interest, and opening this window as wide as possible. But each of these methods has its drawbacks: for instance, increasing imaging time tends to blur the image because the radionuclide migrates in the patient and the patient moves, blurring the image; opening the energy window allows scattered photons to be counted in the wrong pixel, etc.

Thus, known medical imaging systems apportion the available photons among the fewest possible image plane pixels: the image plane of the camera is divided using the largest pixel size that will still permit resolving the smallest features of interest. Indeed, image resolution is often sacrificed specifically to increase the signal-to-noise ratio.

Oversampling

Referring to FIGS. 3a–3c, for the cameras discussed in the following paragraph, the "sampling rate" is the pixel-to-pixel distance at the image plane. Oversampling is accomplished by reducing the pixel size of the image plane, for instance, from the spatial frequency shown in FIG. 3a to that of FIGS. 3b or 3c.

All cameras that respond to individual photons produced by emitters whose operation is totally unaffected by conditions prevailing in any other emitter of the source of flux and have a spatially-quantized output (including Nuclear Medicine cameras, CAT scanners, PET and SPECT scanners, digital radiography devices, CCD-based television or infrared and night vision cameras, but not including, for example, cameras using photographic film, or NMR (nuclear magnetic resonance) and MRI (magnetic resonance imaging) scanners which function by measuring field values instead of discrete particles) have in common the fact that the number of particles collected in a given time in each image pixel is a random variable, usually Poisson-distributed. (To simplify the language of this discussion, we will use the word pixel—which stands for picture element and normally refers to the smallest unit into which a plane image is subdivided—to mean the minimal bin or cell into which a space of any dimension is subdivided.) Further, the pixels' particle counts are pairwise statistically independent, no matter how big or how small the pixels are. From this flow two basic conditions: (1) the noise values associated with any two pixels are pairwise statistically independent, regardless of sampling rate, either temporal or spatial, and (2) as the size of the detector pixels is reduced while increasing the number of detector pixels to maintain a constant detection area or volume, the total noise power, defined as the sum of the count variances, is non-increasing. (In fact, the invention would improve on the current state of the art even if the sum of count variances were slowly increasing.) As a consequence, with increased sampling rate, the total noise power, originally distributed uniformly over one set of frequencies will be spread uniformly over the larger set of frequencies corresponding to the higher sampling rate, while the signal stays confined to its original frequency range. Accordingly, the noise power within the signal band decreases as the sampling rate increases. Thus, band-limiting the oversampled signal-plus-noise combination can reduce the noise, and leave the information-carrying signal substantially unaffected.

Other one-dimensional, or generally, n-dimensional processes that have the same statistical structure (specified by the two basic conditions of the previous paragraph) can also be improved by operating in accordance with the invention.

Reducing cell size (or, equivalently, sampling at a higher temporal frequency) while keeping the total extent of the image area constant, is profoundly counter-intuitive because it reduces the number, n, of photons in each cell, and thus reduces the signal-to-noise ratio=$n/\sqrt{n}$. For instance, if the spatial sampling frequency is increased by quadrupling the number of image plane pixels in both the x and y directions, then each image plane pixel will, on average, count 1/16 as many photons during the image acquisition time, thus reducing the signal-to-noise ratio by a factor of four. This 4x×4y image will be much noisier than the original, possibly to the point of being unreadable were the image to be displayed by conventional methods.

Nevertheless, according to the invention, smaller cell sizes are preferred. A cell size at most half as large as that required to preserve contrast of the finest image feature of interest is preferred. Each factor of two decrease in cell size gives further (though decreasing) benefit, for instance oversampling by factors of four, eight, sixteen, etc. Of course, there may be no point in reducing cell size much below the spacial precision of other components in the camera. In the gamma camera example, for instance, the cell size might be chosen to correspond to the resolution limit of the analog-to-digital converters (ADC's) that read the detector scintillations and produce (x,y) positions for the detected photons. If replacement of the ADC's with higher-resolution ADC's is practicable, then it is desirable to do so, and to reduce the cell size correspondingly.

Ideally, the pixel size is reduced to the limiting condition at which, with probability approaching one, no image plane pixel acquires more than a single photon. The numerical image thus acquired can be filtered through a band-limiting filter and sampled for further use. This displayed image will have a signal-to-noise ratio and a freedom from aliasing arbitrarily close to what it would have been if the image signal had been available for analog band-limiting before being sampled by the discrete-cell detector. Note that in conventional sampling methods, an analog signal is first band-limited and then sampled. In the cameras addressed by the invention, however, this is impossible because an analog signal never exists: the physical events detected are discrete and ephemeral, and are not simultaneously present. By increasing the sampling rate (decreasing cell size) to the point that most pixels count either zero or one events, and storing the results, a good approximation can be formed to having all parts of the image simultaneously present and processable before any sampling takes place. Further, the error in the measurements of the locations of the events is reduced to negligibility.

Though these higher sampling rates are preferred, the invention provides improved images even with relatively modest oversampling rates.

In contrast, the conventional wisdom has been that oversampling had no positive value, and has many disadvantages of which by far the most important is the reduction in signal-to-noise ratio that comes from decreasing counts in pixels. This loss of signal-to-noise ratio is the reason that oversampled images are often unintelligible if displayed using conventional methods.

But if the image is oversampled and properly processed according to the invention, as described below, the result will be better than any image that could be formed from data sampled at conventional rates. This is because in sampling at conventional rates, the power aliased into the signal's frequency band cannot later be removed by any methods known to the prior art.

(According to the present invention, however, much of the aliasing present in any signal acquired by a conventional photon detector can be removed by taking the counts from the coarse grid in which the counts were acquired and randomly redistributing them into the pixels of a finer grid. The ideal, where each cell has at most one count, can be approximated in this way. This method is approximate, in the sense that the result will never be as good as acquiring the image in the fine grid in the first place, but it has been shown to give good results. This result is particularly surprising, in that it contradicts the conventional wisdom that it is impossible to remove aliasing noise caused by improper sampling because the aliasing noise occupies the same frequency band as the signal. The method of this invention can thus be used to improve images acquired by coarse grid detectors, for instance old data in files, or television or night vision data acquired by conventional cameras, for which the preferred acquisition method is not available.

The counts of a coarse pixel can be redistributed into the corresponding fine pixels uniformly. In a somewhat better version, the counts in each coarse pixel can be considered as a histogram bar at the center of the coarse pixel, and a surface can be constructed that smoothly connects the tops of the histogram bars. For instance, a surface can be constructed that connects the count of any pixel to the count of the immediately neighboring pixels. The counts can then be redistributed into the fine pixels with probability weightings proportional to the height of that surface over the fine pixels.)

Band-Limiting Filtering

Various filtering methods can be used to eliminate the noise from the signal, once oversampling has isolated most of the noise to high frequencies. The filter should have a bandwidth at least large enough to include the maximum frequency of the noiseless information, as modified by the camera's optics, but less than that corresponding to the oversampling spacing. After filtering, the signal can be resampled for further use. The resampling spacing should be no lower than one over twice the bandwidth of the band-limiting filter.

Band-limiting filtering may take several forms. Improved images may be obtained by one dimensional filtering, for instance alone scan lines of an oversampled image. Two-dimensional filtering is much more effective, yielding the most noise reduction for a given loss of bandwidth. The invention provides a new class of cylindrically-symmetric Butterworth filters for this purpose, which are much more effective than conventional separable filters.

It was stated earlier that the first step in constructing an image from raw photon counts should be the determination of a count-density function—that is, a function which is non-negative, non-oscillatory, and has the property that integrals of the function over sets of pixels are very nearly proportional to the total number of counts in those pixels. The steps of computing a count-density function and band-limiting can advantageously be combined in a single operation by choosing a band-limiting filter whose impulse response has the required properties The cylindrical Butterworth filters of the invention provide a very good approximation to a desirable count-density function, even though their impulse responses become slightly negative (less than 2% of maximum) over a small subset of their total support.

The filtering may be by either analog or digital methods.

It must be kept in mind that the result of filtering a particular realization of an ensemble—whatever the filter may be—will still reflect to some extent the random deviations of that realization from the ensemble average behavior. Depending on the count density involved, these deviations may be primarily manifested as geometric distortions, or as atypically high or low count values in small regions. In any case, they constitute departures from the invention's goal of delivering a good estimate of ensemble average behavior.

EXSTASE (Extrapolation from Stationary Sets)

Thus, it is desirable to use statistical estimation, possibly in combination with pure linear filtering, to reduce the noise of an oversampled image. In preferred embodiments of the invention, a statistical estimation phase uses prior information about the image-forming system (the camera, the object being imaged, the radiation sources, etc.) and the imaging protocol, to derive from the measured data an improved posterior estimate of the ideal image, which is the ensemble average of the count-density functions obtained in each realization.

Referring to FIGS. 4a–4d, a novel and particularly advantageous estimation method of the invention, called EXSTASE (EXtrapolation from STAtionary SEts), recognizes stationary regions and edge regions. Stationary sets, or stationary regions, are regions of the image where the count density is constant or changes slowly, for instance corresponding to a homogenous organ, and thus where the expected values of neighboring pixels are similar. In images of Poisson count distributions, the variance in counts within neighborhoods of stationary regions is approximately equal to the mean of the neighborhood. Edge regions are regions where the image changes relatively rapidly, and typically form bands separating stationary regions.

Within stationary regions, the prior count density function can be well approximated and there the EXSTASE method uses information from a relatively large neighborhood around the stationary pixel to help estimate the count density function at the pixel. In edge regions, the prior count density function cannot be well approximated, and EXSTASE uses information from a small neighborhood around the pixel to estimate the count density function. In boundary regions between stationary and edge regions, EXSTASE extrapolates information from the stationary region into adjoining edge regions where the count density function is more variable. The effect is to produce a nearly-noiseless image with remarkably sharp transitions and correspondingly-high subjective contrast.

The EXSTASE computation is made more efficient by first taking the data from an individual image (a realization of the ensemble), and producing an improved version more nearly representative of the ensemble as a whole, by detecting and changing atypically high or low values to more-nearly-typical values. This phase identifies outliers and brings them into the normal range in a manner consistent with the ensemble statistics, as these statistics are estimated from the acquired realization. In this manner, the random variations of the photon flux are reduced, to more nearly approximate an orderly flux.

FIG. 4a shows a detail region 400 of the individual detection events of a raw image. Region 402 shows a high density of events (for instance, corresponding to healthy myocardial muscle), and region 404 is a low count density region (corresponding to non-cardiac tissue). In the body, the boundary between the two regions 402 and 404 is sharp: a few cells in width. But because of blurring in the camera "optics" and the fact that the heart is viewed end-on instead of truly in section, the boundary shows up in the image as a gradual edge region 406. In addition, the raw image shows a dark artifact 408, not related to any actual feature of the heart, merely caused by the Poisson randomness in the distribution of the gamma rays. FIG. 4b plots the count density along section line 418 of FIG. 4a, showing a stationary region 422 of high counts, a stationary region 424 of low counts, and an edge region 426. Artifact 408 shows up as a peak 428 in the graph of FIG. 4b. The image plane pixel grid is indicated by hash marks 435: the gamma detections shown as dots are histogrammed into the pixel mesh 435 to form the intensity counts for the final image.

Referring to FIG. 4b, regions of stability are extrapolated into edge regions (as shown by arrows 432 and 434) with an edge 420 and single-pixel noise peaks (arrows 438). The result of this extrapolation is shown in FIGS. 4c and 4d. Note in FIG. 4c that dark region 442,462 (represented by segment 448) has been extended right, and light region 444,464 has been extended left. Edge region 446,466 has been reduced in size, so that the edge (represented at 440) is sharper.

The underlying rationale for the EXSTASE method is based on the following observations. In Nuclear Medicine imaging, the counts collected over some time period are supposed to be used to estimate the mean rate of decay events, and hence the density of radionuclide as a function of position. The actual counts are only an estimate of the distribution that would be measured were the image gathered over an infinite time in an infinite-resolution camera. Current practice simply takes the raw counts as the best available estimate, and ignores prior information available about the physical phenomenon being imaged.

Within anatomical structures, the distribution of radionuclide is fairly smooth over regions larger than the image plane pixel size. At the edges of organs and of lesions, the anatomical edges tend to be fairly sharp, relative to a pixel's width, but the camera's optics and the finiteness of the number of photons that are acquired blur these sharp edges into blurred edges. But the degree of blurring can be measured, both by measuring properties of the camera and by studying images of known objects. These physical properties impart two properties to medical images.

First, images of organs consist of a few relatively-uniform simply-connected regions separated by edge regions (blurred edges of organs). Any small array of pixels lying completely within one of these uniform regions has Poisson-distributed independent counts at each pixel, but the means of these counts differ very little.

Second, because the resolving power of the optics of the imaging system is generally much lower than a single image plane pixel, it is known that a large variation in a single pixel relative to its neighbors is a noise artifact, and not due to the object being imaged. Even a point inhomogeneity in emission from the object necessarily affects several adjacent image plane pixels arranged in a generally-convex shape. The amount of spread that the camera imparts to a point can be measured, and from that information a bound on the maximum difference between two nearby pixels can be derived. Any difference greater than this bound must be attributed to noise rather than to the distribution of the radioactive source.

An image-forming processor can exploit these two known properties to suppress noise and simultaneously preserve contrast. By determining continuous regions of the image corresponding to distinct anatomical features, it becomes possible to distinguish the neighboring-pixel-to-neighboring-pixel value changes that are due to noise from the changes that are due to crossing an image feature boundary. With that information, it is possible to computationally estimate the actual underlying radioemission characteristics of the anatomical structures under study, thus reducing noise.

The EXSTASE method finds relatively stationary regions. For individual pixels within a stationary region that vary from the values of neighboring pixels, the variation is known to be due to noise, and the variant pixel is brought closer to the values of adjoining pixels. However, the contrast is preserved for small lesions, even lesions as small as a single pixel with a "corona" of neighboring pixels whose values have been partially affected. Edge sharpness between stationary regions is enhanced.

FIGS. 5a–5c show the adaptation of the EXSTASE estimator about a stationary region 500 and edge region 501 as it processes three example pixels 512, 522, and 532. In FIG. 5a, pixel 512 is far from the edge region. The EXSTASE estimator can use information from a large neighborhood 514 to estimate the count density at pixel 512. In FIG. 5b, pixel 522 is near edge region 501. A large-diameter neighborhood 524 around pixel 522 would include pixels poorly correlated to pixel 522. Thus, EXSTASE uses a smaller neighborhood 526 that is entirely in the stationary region to estimate the count density for pixel 522. Note that neighborhood 526 is centered at point 528, not 522—the neighborhood may be eccentric about pixel 522. FIG. 5c shows pixel 532 in the edge region 501. EXSTASE uses a very small neighborhood 536 in region 501 to estimate pixel 532 (rather than large diameter neighborhood 534)

Although EXSTASE is a method for statistical estimation, it is clear from FIGS. 5a–5c that in some circumstances EXSTASE can be regarded as an adaptive filter. This identification is favored by the fact that EXSTASE is basically convolutional in nature—EXSTASE scans along an array (two dimensional in FIGS. 5a –5c, but the array could have any dimensionality), and at each point calculates an output value. Whether EXSTASE is regarded as a statistical estimator or as a filter depends on what the main problem with the data in the array is thought to be. If the data are very noisy, then statistical estimation predominates. But if defocusing rather than noise is the main problem, then EXSTASE becomes a powerful deconvolver, because of its inherent edge sharpening characteristics, enhanced by the eccentric feature of EXSTASE, which allows averaging areas to conform more closely to existing edges. A choice between points of view need not be made, because EXSTASE automatically adapts.

If it is known in advance that the data are nearly noise-free, then the deconvolution operation may be enhanced considerably in various ways. The threshold level for distinguishing stationary regions from edge regions may be decreased if there is no noise. Smaller neighborhoods can be used to form the weighted averages, thus preserving smaller features of the image. The set of possible criteria used for detecting change can be enlarged, for instance to include using derivatives in detecting edges and changes, thus adding more sensitivity to edge detection.

Implementations of Band-Limiting Filtering and EXSTASE

FIG. 6a presents a pseudo-code description of an image-formation program that exploits these physical realities and image properties.

Before entering the pseudo-code of FIG. 6a, a photon flux has been acquired by using pixels or bins much smaller than the spatial distance required by the Nyquist sampling theorem for the information. For instance, if the collimator has blurred the image so that the finest feature preserved at the image plane is 8 mm wide, then the detector cell size dimension should be at most 4 mm to preserve contrast of the smallest features of interest. Preferably, the sampling is at least twice this, one detector per 2 mm in this example. More preferably still, the detector cell size corresponds to the lossiest component further downstream in the camera (where the "camera" includes the detector crystal, the photomultiplier tubes 108, the analog-to-digital converters that convert the scintillation location in crystal 106 to a numerical representation, or the representation used to store the detection location of the event in the computer's memory).

The filter parameters in steps 610, 630, and 652 are determined by two physical factors: (1) the width of the pulse-spread function (PSF) of the imaging system, which is a composite of the defocusing effects of the camera, including, in particular, the collimator, and the camera-to-organ distance; and (2) the photon density per unit area in significant portions of the image, because the fewer photons there are, the more defocused the image will seem. In the example of FIG. 6a, the parameters are examples of those that might be used with a gamma camera for imaging the heart, where an image plane of about 25 cm square is divided into 256×256 pixels. For this subdivision of the image plane, the full-width-at-half-maximum (FWHM) of the pulse spread function of the imaging system is about 12 pixels.

In step 610, the raw image $X_0$ is filtered through a two-dimensional, cylindrically-symmetric Butterworth filter, to produce $X_1$, a very wide-band estimate of the countdensity function. The half-power point of the frequency transfer function of this filter is 30. (This discussion of frequency functions of sampled systems uses the conventions of W.H. Press et al., *Numerical Recipes in C*, 2nd Ed., Cambridge University Press, New York, 1992, pp. 510–591, especially equation 12.1.5, which defines the normalized frequency scale used in those conventions. The number 30 used here, and the values 20 and 13.5 used in later filtering steps 630 and 652, represent, for an image with N=256 pixels/side, the fraction 30/(N/2) times the maximum frequency. The latter is given by ½s, where s is the width of a pixel measured in whatever physical units are convenient.) Conceptually, the photon arrival markers are converted into a count density function: each marker is replaced by the two-dimensional impulse response of the filter, centered on the marker This "filter" as discussed earlier, simultaneously constructs a count-density function and performs band-limiting. The width of the impulse response of the filter is chosen to be on the order of the maximum distance between nearest-neighbor markers in significant portions of the image. This can be measured in each image to be processed, but a good rule of thumb it to make the width (FWHM) of the spatial impulse response of the filter about ¼ the width (FWHM) of the spatial pulse-spread function of the imaging system. (The description of the system in terms of relative PSF widths is preferred because it lends itself naturally to making the entire filtering and/or estimation system adaptive, if desired. It is very easy, using any of many procedures known in the art, to estimate the width of the PSF of the combination of camera and information in any given instance, after the data have been acquired. In an adaptive situation, that is all that is needed.)

Step 620 further reduces noise by searching for the pixels most likely to contain outliers, and conforming these noisy pixels to their surrounding pixels. This step is not strictly necessary, since the remainder of the EXSTASE method will similarly reduce outliers, but reducing outliers at this stage helps to reduce overall computation time. Step 620 has two substeps. At each pixel, substep 622 selects a neighborhood of surrounding pixels and computes the mean and standard deviation of the pixels in the neighborhood. Step 624 flattens any outliers outside a given range about the mean: for instance, any pixel outside ±1.5 standard deviations is clipped to the mean ±1.5 standard deviation. The value for K (1.5 in this case) will be determined by the largest change in pixel-to-pixel value expected in a noise-free image.

The neighborhood chosen in step 622 will vary with the size of the incoming $X_0$ pixels, relative to the FWHM of the PSF of the information. For instance, if the FWHM is 3 or 4 pixels, the chosen neighborhood may be the 3×3 array of pixels centered on the pixel of interest. If an image which is conventionally acquired at 64×64 pixels is in fact, according to this invention, acquired at 256×256 pixels, so that the FWHM of the information is roughly 12 pixels, then it may be preferred to use a 7×7 square around the pixel of interest, or the edge pixels of a 7×7 square centered on pixel (i,j).

Further, in step 622 it may be desirable to discard the outliers from the neighborhood before computing the mean and standard deviation of the remaining pixels. In a 64×64 Nuclear Medicine image, it is known that the collimator will blur the image to an extent where, even if the true density of the nuclide dropped from full scale to zero precisely on a pixel boundary, the corresponding raw counts would only drop by, for example, 12%, depending on the collimator. Thus, any variation greater than 12% is known to be due to noise. Further, in a stationary region, it is desirable to limit outliers sharply in step 624, for instance to within 1.5 standard deviations of the mean. In a normal distribution, about 14% of a population will lie outside $\mu \pm 1.5\sigma$. Thus, if pixel $X_1(i,j)$ is an outlier, there could easily be a second outlier in the eight-pixel ring around pixel $X_1(i,j)$. Half the time, these two outliers would point in the same direction and thus protect each other. To minimize this possibility, step 622 may exclude the lowest and highest $X_1$'s before computing the mean and standard deviation of the neighborhood.

Step 630 filters the results of step 620 using a cylindrically-symmetric Butterworth filter with half-power frequency equal to 20 to form a revised estimate $X_3$ of the count density function. Filtering step 630 (and step 652 as well) forms weighted averages over sets of pixels surrounding each pixel. This filtering reduces false edge detection (false edges correspond to noise rather than information) in subsequent edge-detection steps, reducing unnecessary computation. The averaging weights are given by the impulse response of the cylindrical Butterworth filters of steps 610, 630, and 652, shown in cross section 672, 673, 674 in FIG. 6b. For instance, the filter 673 with cutoff frequency 20 has a spatial full-width-at-half-maximum (FWHM) of about four pixels (note that the figure shows only half of a two-sided symmetric function), and pixels at a diameter of ten pixels still have significant weights. Filter step 630 reduces some of the low-contrast noise that escaped the outlier flattening of step 620, and brings the bandwidth of the image somewhat closer to the information bandwidth. Recall that the information bandwidth of the image has a spatial FWHM at roughly 12 (the FWHM of the camera), or about three times the spatial FWHM of the filter of step 630.

Step 640 categorizes the pixels as belonging to either "stationary sets" or edge regions, in two substeps. Substep 642 selects a neighborhood of pixels around each pixel, and computes two arrays whose entries are, respectively, the means and variances of the corresponding neighborhoods in $X_3$. The neighborhoods of step 640 may be the same as those used in step 622, or may be different. Substep 644 computes an array of boolean values "is_an_edge," whose entries are true in entries corresponding to edge regions of the original image, and false in entries corresponding to stationary set pixels. At point 648 of the program, the array "is_an_edge" looks like a line drawing of the scene, with true's at edge points (areas of rapid change of the original grey-scale image $X_0$) and false's in stationary regions.

Up to this point, the method of FIG. 6a has done its computation in floating-point, reflecting the fact that the results are to be used in further computation. Step 650 produces an array $X_4$ in an integer representation appropriate for a display monitor, for instance in the range 0 to 255. Array $X_4$ is the method's final estimate of the count density function at each pixel.

In step 650 (with its substeps 652, 654, and 656), if the pixel is in a stationary region, the value of the final image pixel is estimated as a local average of pixels in a neighborhood. This local average may be computed in any of a number of ways; the example of step 652 filters image $X_3$ through a cylindrically-symmetric Butterworth filter with half-power frequency equal to 13.5. This filter does spatial averaging that will be used to give an estimate of the ensemble average in stationary areas. The filter has a FWHM of six pixels, which is still only half the FWHM of the information. It is desirable to make this filter impulse response as wide as possible, but if it is made too wide, it will start to blur features. Referring again to FIG. 6b, the net effect of the FWHM 30 filter 672 of step 610, the FWHM 20 filter 673 of step 630, and the FWHM 13.5 filter 674 of step 630 is a filter 677 of FWHM 8 pixels, roughly ⅔ the information FWHM 678. This is the preferred compromise.

Returning to FIG. 6a, step 654 tests an entry of the "is_an_edge" array; if the pixel is found to lie in a stationary region, the local average value computed in step 652 is copied by step 656 to $X_4[i,j]$.

Step 660 computes $X_4$ for pixels not in stationary regions. The general principle in step 660 and its substeps 662–666 is to examine the neighborhood of pixel (i,j) to determine where there are stationary regions and where there are edge regions. If pixel (i,j) is surrounded by edge pixels, then very little information is available to improve the value of the pixel, and thus any adjustment should be minor and based only on immediately adjoining pixels.

On the other hand, if pixel $X_3(i,j)$ is an edge pixel with a nearby stationary region, a value of pixel $X_4(i,j)$ can be computed as a function of the pixels in the nearby stationary region.

The rationale and computation of step 660 are as follows. (Note that if the pixel is in a stationary set, the value was determined in step 650; thus step 660 only deals with edge pixels.) As shown in the comment for step 660 of FIG. 6a, the program examines eight vectors, each comprising three adjacent pixels extending in the eight primary directions from the pixel under consideration. If all eight of the vectors contain at least one edge pixel, then pixel $X_3(i,j)$ is known to be in a region of rapid transition far from a stationary region, and therefore relatively little information can be extrapolated from the surrounding pixels. For these pixels, step 662 computes $X_4(i,j)$, estimating the count density function at pixel (i,j), by the mean of the nine pixels in the square neighborhood centered on $X_3(i,j)$, further reducing noise. Because the value for pixel $X_4(i,j)$ is computed from a small neighborhood around pixel $X_3(i,j)$ that does not extend outside the edge region, this averaging does not reduce edge sharpness.

Alternately, at step 664, if at least one of the eight vectors contains no edge pixels, then it is known that $X_3(i,j)$ is "near the edge of an edge:" there is an adjoining stationary region in at least one direction. The actual tissue that was imaged in this pixel really belonged to the same anatomical structure as the neighboring stationary region, and the difference in this pixel from the pixels in that stationary region is due only to blurring by the optical system. Thus, a new value of $X_4(i,j)$ extrapolated from the values of the nearby stationary pixels is likely to be a better estimation than the raw counts of pixel $X_3(i,j)$ of the true radionuclide distribution in this tissue. The extrapolation may be by any of a number of reasonable computations. One such reasonable computation, shown in substeps 664 and 666, finds the variances of the values of each of the vectors with no edge points; the new $X_4(i,j)$ is computed, at 688, by linearly extrapolating from a linear or quadratic fit to the stationary-set vector with the lowest variance.

FIG. 6a omits details of the implementation that would be well-understood to one of ordinary skill. For instance, if the computation of a property of a pixel X(i,j) depends on pixels in a 7×7 box surrounding the pixel, then the property cannot be computed by the normal method for those pixels in the three rows and columns at the edges of the image array. It may be desirable to estimate the property using a different collection of pixels, for instance only the portion of the 7×7 box that actually lies in the image array. Or a program may simply omit computing the property at the edge of the image, since the camera operator endeavors to center important features in the field of view, far from edges, so that nothing useful is found near the edges.

The neighborhoods of FIG. 6a may either have sharp edges (for instance, 3×3 or 7×7 boxes) or edges that tail out, with diminishing effect, over many pixels (like the Butterworth filters of FIG. 6b).

FIG. 7a shows an alternate embodiment of discriminating the image into stationary and edge regions, and extrapolating from the stationary regions into the edge regions. The method 700 of FIG. 7a, which we will refer to as "Adaptive Bayesian", can be used with images that were acquired with conventional, mildly-oversampling or oversampling cameras, but not band-limited, provided the counts per pixel in important areas of the image are in the order of 50–100 or greater. The method of FIG. 7a is considerably faster than the method of FIG. 6a. FIG. 7a assumes its input is in $X_2$, and its output in $X_4$ for consistency with the discussion of FIG. 6a.

In step 702, values are chosen for tunable parameters $\alpha_0$ and $\alpha_f$. These values will be used in steps 720, 726, 728, 732, and 734 as described below. $\alpha_0$ is fixed by the imaging protocol in use, being equal to the ratio (photons to be acquired for an image)/(photons conventionally acquired). Values $\alpha_0=0.5$ and $\alpha_f=0.5$ have been tried and found to give very good results, much better than conventional images, and correspond to the case where the number of acquired photon is ⅓ of the number conventionally acquired. (See the appended "Notes on Non-Linear Estimation".

Step 704 flattens outliers, for instance using the method of step 620 of FIG. 6a.

Step 710 computes the mean "mu" and sample variance "v" for a neighborhood around each $X_3$ pixel, for instance the 3×3 neighborhood with the pixel itself, the highest neighbor, and the lowest neighbor excluded. (The neighborhoods of step 710 may be the same as those used in FIG. 6a, or may be different.) From these means and variances, step 712 computes an estimate for a property α for each pixel:

$$\alpha[i,j] = \frac{(N-3)}{N} \times \frac{mu[i,j]}{v[i,j]}$$

where N is the number of pixels in the neighborhood used to compute mu and v. α is a measure of the correlation between the ensemble mean of a pixel's value and the ensemble means of neighboring pixels. α[i,j] estimates the stationarity of the pixel relative to its neighborhood, and thus the amount of knowledge available about the ensemble average ascertainable from the neighboring pixels. α will lie between zero and roughly 1.25, with high values indicating stationary regions (where a pixel's ensemble mean is strongly correlated to the ensemble means of its neighbors) and low values of α indicating edge regions where the ensemble mean varies rapidly.

Step 720 selects a neighborhood of α's around α[i,j], for instance the 3×3 neighborhood surrounding α[i,j], including α[i,j]. These neighborhood α's are compared to a threshold value $α_t$: if all neighborhood α's are greater than $α_t$, the pixel is regarded as being in a relatively stationary region. (Again, the choice of the neighborhood used in steps 720–734 is independent of the choices in FIG. 6a or steps 710–712—they may be the same neighborhoods, or they may be different.)

Steps 724, 728, and 734 each compute estimated values of $X_4[i,j]$ by forming a weighted average of pixel $X_3[i,j]$ with its neighboring pixels. The weights for the weighted average vary over the image with local properties of the image. For instance, in regions where the image is stationary and variations are more likely to be due to noise than to actual variations in the underlying count density, the estimate computed for $X_4[i,j]$ is weighted more heavily toward the neighborhood and less toward the value of individual pixel $X_3[i,j]$. On the other hand, in regions where the image is changing rapidly, the method weights the neighborhood lightly and the individual pixel more heavily. The weighting factor is parameter α computed in step 712.

In step 722, if all neighborhood α's are greater than or equal to $α_t$, then it is known that the entire neighborhood is fairly stationary, with perhaps a gently-sloping gradient with less than 5% contrast across the neighborhood. Any of the surrounding α's and mu's could serve to estimate $X_4[i,j]$, but it is best, in step 724, to use α[i,j] and mu[i,j] to avoid contouring artifacts.

In step 726, if all neighborhood α's are below $α_t$, then it is known that the entire neighborhood is a region of rapid gradient in the ensemble average, that is, an edge region. (Other possibilities are precluded by the blurring of the camera and the outlier flattening of step 704.) In this case, the computation of $X_4[i,j]$ depends almost entirely on $X_3[i,j]$ with very little weight given to the other pixels of the neighborhood. Because the pixel is in a rapidly-varying region, the α[i,j] calculated in step 712 of $X_4[i,j]$) is a poor estimate of the actual value of α at the pixel (recall that α is a measure of the correlation of ensemble averages of pixels in a neighborhood). Thus, in these regions, step 728 uses $α_0$ (chosen in step 702) to form $X_4$.

Step 732 is reached when either (a) pixel $X_3[i,j]$ is an outlier that slipped though step 704, or (b) pixel $X_3[i,j]$ lies on the boundary between a stationary region and an edge region, or (c) pixel $X_3[i,j]$ is a small lesion with a surrounding corona of partially-affected tissue. Removing an outlier (case a) is similar to the effect at boundaries (case b), and thus these two cases are discussed together.

Referring to FIG. 7b, consider a large-area edge region, shaded region 740. The neighborhood 744 centered on pixel $X_3[i,j]$ 742 is half in the stationary region to the left, and half in edge region 740, and it may have a low α[i,j], though not necessarily. Neighborhood 746 almost certainly has a low α[i−1,j+1], while neighborhood 748 almost certainly has a high α[i+1,j−1]. The effect of step 734 is to estimate a value for pixel $X_4[i,j]$ using the mean for neighborhood [i+1,j−1] 748. Hence, the effect is to extend the stationary region as far as possible into the edge region, thus narrowing the edge region by about 1 pixel from the left end. The same thing happens when computing $X_4$'s on the right end of the edge, so that the edge region, which starts being perhaps four pixels wide (more for the endocardial surface of ungated thallium scans) is narrowed by two pixels—a considerable sharpening. Curve 750 suggests what would have happened if, instead of the computation of step 734, the program had instead used the mu and α for pixel [i,j] when computing $X_4[i,j]$: the value would have been lower, point 752, than the value obtained by using neighborhood [i+1,j−1] 748, point 754. That is, using the α and mu for neighborhood [i,j] 744 would have further softened the edge, just as a linear filter would do.

Referring now to FIG. 7c, consider the effect of step 734 on a minimal lesion 770, the intensity of shading indicating size of the discrepancy between the lesion count and the surround. The counts of lesion 770 have been spread essentially throughout neighborhood [i,j] 772 by de-focusing of the collimator, etc. Threshold $α_t$ is specifically chosen so that neighborhood [i,j] 772 will have an α[i,j]≧$α_t$. Neighborhood [i+1, j−1] 776 will almost certainly have a lower α, because it is less homogeneous, lying on the steeply-falling portion of the spread. Thus, $X_4[i,j]$ will be estimated using the mu and α of neighborhood [i,j] 772, and will thus have nearly the same contrast it had to begin with.

Pixel 774 has an inhomogeneous neighborhood 776, and hence an α<$α_t$. All its neighboring neighborhoods also have low α's except neighborhood 772 (the neighborhood centered on the lesion), and possibly neighborhood 778, which is mostly in the stationary region. The mu of neighborhood 772 will often be closer in value to the count at pixel 774, so that the estimate of the count of pixel 774 will often be raised to resemble more closely the mid-lesion value. Thus the effect of the estimation will often be to enlarge the minimal lesion somewhat, and with near peak contrast, thus enhancing its visibility.

If the contrast of lesion 770 is so low that neighborhood 772 all its neighboring neighborhoods have α's greater than $α_t$, then step 724 is executed (the value of the lesion pixel is estimated using the mu and α for the lesion-centered neighborhood), and thus the pixel substantially retains its original contrast. In computing $X_4$ for pixel 774, if contrast is so low that all arrays have α≧$α_t$, then step 724 is executed for pixel 774. The mu value for neighborhood 778 may often be closer to the value of the stationary surround than is the $X_3$ value of pixel 774, and the result is to reduce lesion visibility somewhat.

All this points up the importance of setting the threshold $α_t$ properly. Alternate rules to steps 724, 728, and 734 can reduce the dependence on a good choice of $α_t$. In constructing alternatives to steps 724–734, a main goal is to ensure that something like step 734 exists and has a high probability of being used for pixels located near edges or small lesions.

In a first alternate, of the nine neighborhoods including pixel $X_3[i,j]$, identify, say, the four with the largest $\alpha$'s, and from among these four choose the neighborhood $[i_0,j_0]$ whose $mu[i_0,j_0]$ is closest to $X_3[i,j]$. If that $\alpha[i_0,j_0] \geq \alpha_0$, use $mu[i_0,j_0]$ and $\alpha[i_0,j_0]$, or else if $\alpha[i_0,j_0] < \alpha_0$ use $mu[i,j]$ and $\alpha[i,j]$ to estimate $X_4[i,j]$.

This first alternate could be modified somewhat, to include the benefits of step 724, to form a second alternate: of the nine neighborhoods associated with pixel $X_3[i,j]$, identify the neighborhoods with largest $\alpha \geq \alpha_0$. If at $X_3[i,j]$ all nine $\alpha < \alpha_0$, use $mu[i,j]$ and $\alpha$ to estimate $X_4[i,j]$. Otherwise, among the four neighborhoods with the largest $\alpha \geq \alpha_0$, choose the neighborhood $[i_0,j_0]$ whose $mu[i_0,j_0]$ is nearest $X_3[i,j]$, and use that $mu[i_0,j_0]$ and $\alpha[i_0,j_0]$ to estimate $X_4[i,j]$.

Note that using the $mu[i_0,j_0]$ closest to $mu[i,j]$, or the neighborhood centered on $X[i,j]$, are expressions of conservatism. In the first instance, the image is changed as little as possible. The second instance exploits the probability that the average of counts on the ring of pixels around $X[i,j]$ is probably the most accurate estimator of $X_4[i,j]$ except near edges, where the ring is not homogenous. A different kind of conservatism is expressed by arguing that the neighborhood with the biggest $\alpha$, especially if $\alpha > \alpha_0$, is probably the most noise-free, and since $X[i,j]$ belongs to this low-noise neighborhood, maybe $X_4[i,j]$ should be estimated from this smoothest neighborhood. Following this philosophy, a very simple third alternate can be constructed as follows: to estimate $X_4[i,j]$, pick the $i_0$ and $j_0$ with maximum $\alpha$. Use $mu[i_0,j_0]$ and $\alpha[i_0,j_0]$ if $\alpha[i_0,j_0] \geq \alpha_0$, or $mu[i,j]$ and $\alpha_0$ if $\alpha[i_0,j_0] < \alpha_0$.

Finally, the third alternative can be modified to form a fourth alternate with most of the content of original steps 724 and 728. Pick $i_0$ and $j_0$ to be the $i,j$ in the neighborhood of $X[i,j]$ with the largest $\alpha[i_0,j_0]$:

(a) If $\alpha[i_0,j_0] \geq \alpha_0$, and if $\alpha[i,j]$ satisfies:

$$\left| \frac{\alpha[i_0,j_0] - \alpha[i,j]}{\alpha[i_0,j_0]} \right| < 0.15$$

then use $mu[i,j]$ and the larger of $\alpha[i_0,j_0]$ and $\alpha_0$ to estimate $X_4[i,j]$.

(b) If the inequality is not satisfied, use $mu[i_0,j_0]$ and $\alpha[i_0,j_0]$ to estimate $X_4[i,j]$.

(c) If $\alpha[i_0,j_0] < \alpha_0$ use $mu[i,j]$ and $\alpha$ to estimate $X_4[i,j]$.

Consider how alternate rule four (or even the original set of steps 724–734) fails if $\alpha_0$ is chosen too high. In that case, it will be true for most pixels that the largest neighborhood $\alpha$ is less than $\alpha_0$, and thus alternate rule four confines itself to using the $mu[i,j]$ for neighborhood $[i,j]$, and the constant value $\alpha = \alpha_0$ to estimate most of the $X_4$'s. In other words, the estimation process degenerates to convolving the image with a linear filter that does uniformly-weighted local averaging. The failure is not catastrophic, even if the number of acquired photons drops farther than expected.

The radiologist may want to alter the value of $\alpha_0$, and the corresponding protocol, for instance, to eliminate excessive smoothing.

Further Refinements Enabled by the Invention

With the oversampling-and-band-limiting technique, and using EXSTASE to estimate the ensemble average, a number of further refinements that have desirable properties become practical in forming images. Because these techniques reduce the number of photons detected and thereby reduce the signal-to-noise ratio and soften edges, they have not typically been used in forming images by conventional means. Referring again to FIGS. 9a–9d, the invention can form better images from fewer photons, and thus these photon-selecting techniques become practically useful in further improving images. These refinements, each of which is discussed in more detail below, include (1) using physiological gating, (2) choosing to count only photons with good imaging properties, even if the chosen photons are less abundant than other available photons, discussed in connection with FIG. 8, and (3) using higher resolution collimators. A fourth technique, using higher exponents in converting counts to displayed color values, does not reduce photon count, but is not used in conventional images because it amplifies noise present in them.

The probability of detecting a lesion improves with the square of the contrast, and worsens linearly as the count density decreases. Each of these refinements improve contrast within the imaging system or take advantage of physics external to the camera to enhance contrast and/or reduce blurring. The enhanced contrast produced by these improvements, together with the virtual elimination of noise though oversampling and EXTASE, greatly increases detectability of lesions.

The invention allows the image to be acquired with physiological gating. In respiratory gating, the patient's breathing is monitored, and the counting of photons is suspended during the time the chest is moving, typically about half the respiratory cycle. But because it discards half the photons, this technique has had a high error rate and thus is not used with conventional image forming techniques. Because the invention can overcome this reduction of photon counts, gating can be used to remove the blurring effects of respiratory motion. Respiratory gating is particularly useful in lung, heart, and liver scans.

FIG. 8 shows the gamma spectrum 800 of $^{201}$thallium. A myocardial perfusion Nuclear Medicine scan typically images the 76–83 KeV gamma rays by centering the energy window 804 of the gamma camera on the photopeak 806 of the 76–83 KeV gammas. The invention allows the window to be set at a range 808 above the photopeak, for instance 10% above. In the higher window, the ratio of primary (unscattered) photons to scattered photons (photons that have been deflected inside the patient) is higher than in the window surrounding the photopeak. Thus, the higher window reduces the effect of scattered photons and increases image contrast, and greatly increases the detectability of small lesions. Because this refinement reduces the number of photons counted in each pixel (by a factor of two to four depending on the organ being scanned), the signal-to-noise ratio decreases by a factor of 1.4 to 2, a result that renders the higher energy window unusable with conventional methods of forming an image.

This energy window refinement is particularly advantageous in cardiac blood-pool studies, which are done with the $^{99m}$Tc isotope, because scatter effects give misleadingly low estimates of cardiac ejection fraction in all but very thin-chested patients, and ejection fraction is a principal prognostic indicator, and thus the most important reason for doing the study in the first place.

Also shown in FIG. 8 is a smaller gamma peak 820 at 167 KeV. Though 167 KeV photons are only about 11% as abundant as the 76–83 KeV photons, their higher energy reduces the proportion that is absorbed as they pass through overlying tissue. Thus, by the time these photons reach the gamma camera, they are typically about 20% as abundant as the 76–83 KeV photons. Being able to form an intelligible image from 167 KeV photons is particularly advantageous in patients with fat breasts, or in cases where the heart lies behind a high-arched diaphragm, because the relatively higher absorption loss of 76–83 KeV photons produces, misleadingly the appearance of lesions in the myocardium, hence producing false positive lesion detections. Again, it is advantageous to set the energy window 822 slightly above the photopeak of the 167 KeV gamma. The invention overcomes the factor of $\sqrt{5}$ drop in signal-to-noise ratio that makes the 167 KeV photon unacceptable for imaging by conventional techniques.

Because photon count falls with collimator resolution, conventional Nuclear Medicine image formation methods require low resolution collimators to obtain readable images. Low resolution is the principal defect of Nuclear Medicine and, for organs near the body surface, may be corrected by use of higher resolution collimators. The invention allows, for instance, doubling collimator resolution and accepting the attendant ¾ drop in the number of photons counted. This improves resolution of the camera as a whole, reducing false negative detections, particularly of small lesions.

Contrast may be increased by raising pixel image values to a power greater than one, but this also magnifies noise. With the nearly noise-free images produced by the invention, this power feature becomes useable. Because subjective contrast falls with increasing image display size, this technique is particularly useful in displaying magnified images.

The choice of which of these techniques to use in which combination depends on the purpose of the imaging. For instance, in imaging to detect reduced myocardial uptake or a small tumor (both of which produce a "cold spot" in the image), a group of techniques would be chosen to improve contrast, for instance windowing on the higher-energy photon. In a study of cardiac wall motion abnormalities, the techniques chosen would be those that improve sharp definition of the myocardial wall, for instance respiratory gating.

Displaying the Image

The image values produced by oversampling and bandlimiting, with or without EXSTASE, and also the image values produced by the Bayesian estimation procedure (the $X_4$'s produced by the methods discussed in FIGS. 6a and 7a) must, conservatively, be thought to include some error, the unpredictable error normally described by the variance associated with any estimation procedure that starts from noisy data. In other fields unrelated to imaging, it is customary to plot data estimated or measured from a noisy source by showing error bars at each value, to remind the viewer of the possible range of error of each measurement and to discourage the viewer from interpreting small rises and drops in measured values as significant, when in fact they might be well within the uncertainty of the measurements.

There is no widely-accepted method analogous to error bars for use with images. However, with the relatively noise-free images provided by the invention, even tiny errors, when they occur in close proximity to each other, form very low-contrast blobs which can be very visible and could be confused with real features. It is therefore desirable to devise analogous "error bars" for the displayed pixels of an image. The key to devising a practical solution, which preserves the clarity of the image while at the same time preventing the viewer from over-interpreting small random features of it, departs from the observation that the contrast level of the random imperfections is of the order of 2% or less, a level which is far below what can be detected in conventionally-acquired images where, owing to random fluctuations in the counts per pixel, a contrast level of 6% to 8% is the minimum that can be detected reliably for small features. The method used in the preferred embodiment is to add to each image value artificially-generated random noise of a particular character and in the amount appropriate to each image value. The special features of the noise are determined by analogy with error bars. Thus, if the variance of the estimation were $\sigma^2$, the error bars might span an interval $\pm\sigma$ around the estimated value. Thus the noise should have limited amplitude determined by the estimation variance at each pixel, and of course it should be independent from one pixel to the next. Adding noise uniformly throughout an image is found, however, to compromise the subjective sharpness of the edges. It has been found that a good compromise between achieving the effect of error bars and achieving sharp edges, is to add the artificial noise only to a subset of all pixels, typically to ¾ of the pixels. The unaffected subset of pixels can be chosen at random, but doing so is time-consuming, and has been found to be indistinguishable from simply choosing any uniformly-distributed subset of pixels, for example, all pixels for which both row and column indexes are even numbers. Thus the preferred preparation of images for display, in cases where the inclusion of error bars is thought useful, is embodied in the following lines of MATLAB code, in which $X_4(i,j)$ denotes the estimated values (for instance, as computed in FIG. 6a or 7a), and $X_5(i,j)$ denotes the values to be displayed, and the function rand produces a new random number, independent and uniformly distributed in (−1,1), each time it is invoked:

```
for i=1 to imagesize
    for j=1 to imagesize
        if rem(i,2)==0 & rem(j,2)==0 then
            X₅(i,j)=X₄(i,j);
        else
            X₅(i,j)=(X₄(i,j)^0.5)*rand*beta+X₄(i,j);
        end %if
    end %n
end %m
```

The factor beta is in the range [0,1] and, while its value is usually 1, it can be selected to be less if the count density in a particular imaging procedure is high enough, or if the use of error bars is less critical. This procedure is particularly useful to expand image size without the smoothing implicit in conventional interpolation procedures.

Another method of adding "error bars" to the displayed pixels, for use with the method of FIG. 7a, exploits the display capabilities of a CRT, compared to the traditional method of producing a static image on paper or film. Rather than taking the information-destroying step of choosing the mean of the computed posterior probability distribution of the value at each display pixel, this method varies the brightness of the CRT pixels, with values chosen in accordance with the distribution function determined for that point. The result is a static image viewed in a live mode, and if the rate of variation is chosen properly, the live image gives the human brain's pattern recognition mechanism the opportunity of making a final determination, which may lead to more subtle discrimination than simply choosing the mean of the distribution at each pixel.

Clearly, the rate of variation must be slow enough so that the eye is not presented many different values for any given pixel within one retinal-retention integration time of the eye, else the result would be not much different from simply displaying the mean of the distribution at each pixel statically. However, the viewer may be provided options to speed up the random variation or to replace the image with a pre-computed image of distribution means.

It may be desirable not to vary all pixels in step, but rather to select pixels to be varied at random, fairly large numbers at a time (perhaps ¼ of the total population at a time) and to flatten outliers, for instance as shown in steps 620 or 704 of FIGS. 6a and 7a. The viewer may have the option to freeze the live image, thus to capture in static form any image along the way that captures his interest.

Other Implementation Issues

There are two major implementation issues: obtaining oversampled data, and the computational demands of the band-limiting filtering and EXSTASE estimation.

Conventional detectors may need to be modified for optimum use with the invention. CCD cameras would need to be redesigned with more, smaller cells. This is also true for PET and CAT scanners, which have discrete detectors. Geiger counters may be modified by reducing the integration intervals during which photons are accumulated.

A gamma camera for Nuclear Medicine may be modified for use with the invention as follows. Each gamma ray detected is originally generated as an analog (x,y) output value, which is digitized by analog-to-digital converters. Conventional gamma cameras quantize these analog values to six or seven bits (64×64 or 128×128 levels) and then store the information by incrementing the value of a RAM cell corresponding to the location of the detection. To carry out the invention, the analog-to-digital converters could be upgraded, for instance to ten bits, giving 1024×1024 quantization. It is desirable to acquire the data in list mode, in which the camera reports a 3-tuple of time, x, and y for each observed photon. Ideally, the cell size of the acquisition is reduced to the limiting point at which, with probability approaching one, no image plane pixel acquires more than a single photon, though the invention gives good results before that limit is reached. The photon events may either be recorded in an array of RAM cells corresponding to image plane pixels, or may be stored as a list of discrete events. The latter storage scheme is required if the times of events are to be stored with events' locations, for possible respiratory or cardiac gating, or in connection with regularizing the photon flux.

Reduced cell size will generally increase the cost of the imaging system as a whole, because of increased cost of the fine cell detector itself, increased memory use for storing the counts, and increased processing power required to form an image. For instance, a conventional 64×64 cell gamma camera, with two bytes per cell of storage, requires only 8K of storage. The same data, acquired into 1024×1024 cells with one byte per cell, requires one megabyte. As the cell size is decreased to approach the case where most cells count only one photon, it becomes desirable to store the counts in list mode rather than storing them in memory cells laid out corresponding the image plane cells. The highest oversampling rates would typically be used in applications where the cost of misreading an image is high, for instance in battle tank imaging systems or in diagnosing life-threatening diseases from medical images.

The computation time for Nuclear Medicine images should be kept in the range of thirty to sixty seconds per image. Because the statistical estimation portion of the process is convolutional and non-linear (and thus has to be done without benefit of the Fast Fourier Transform), the computational demand may require special purpose hardware. Ideally, a high-speed computer module (e.g., an array processor) would be attached to each camera, and its output can be networked to standard Nuclear Medicine workstations with which physicians are already familiar.

In high-count images, for instance television images, the noise levels may be sufficiently low that the EXSTASE statistical estimation method may not be needed. Rather, less-demanding band-limiting filtering may be substituted to obtain substantial improvement in image quality at lower computational cost.

Other Applications

The invention is useful in cases where the particles are emitted from the interior of the object being imaged (for instance, Nuclear Medicine), or reflected from or emitted at the surface of the object, or differentially transmitted through the object (for instance, X-ray photography).

The invention is useful with detectors whose cells are discrete, in the special case of images, called projections, used in any dimensionality, either spatial or temporal. For instance, in tomography, the cells might be three-dimensional volume elements. In monitoring a nuclear reaction, the cells may be one-dimensional time intervals. In Nuclear Medicine images of the heart, the cells have two spatial dimensions and one time dimension so that a moving image of the beating heart can be produced.

It has been found that, in tomographic reconstruction by the standard filtered back-projection method, the usual one-dimensional filtering before back-projection should always be replaced with two-dimensional filtering of each projection. This is even more advantageous if one uses an oversampled grid with cylindrical band-limiting, followed by EXSTASE estimation, though this last step can often be omitted.

In television and night vision devices, it is sometimes desirable that oversampled acquisition, band-limiting filtering, and subsequent resampling to display an image all happen in real time.

The method of this invention includes making detectors with very small cells and bandlimiting the data derived from the detectors. But bandlimiting is a special case of a more general method, which might be called mixing, and which may take place either at the input to the detector, or at the output from it, or as part of the structure of the detector itself. One example of mixing has already been described, the bandlimiting-EXSTASE method of FIGS. 6a and 7a. Other methods are described below.

In applications where the photon detector and the display device are substantially in the same place and the signal need not be transmitted over a limited-bandwidth channel (for instance, a night vision device inside a tank, or a television unit for semi-automatic manufacturing inspection), an oversampling CCD unit can be used to acquire data. The viewing monitor itself can act as a band-limiting low-pass filter, if the phosphor has the appropriate persistence, merely by adjusting the monitor's beam cross section to have a width greater than the beam width that would be needed to display the oversampled signal without loss of display resolution. The image displayed on the monitor would have about the same resolution as that made with a conventional CCD, but much less aliasing and noise. As usual for this invention, the improvement can be apportioned between improved signal-to-noise ratio and improved resolution by adjusting the beam cross section and phosphor persistence.

Mixing at the detector itself—for example, on a CCD—depends on there being leakage of charge from each cell to surrounding cells. Capacitive leakage exists on every CCD and great efforts are expended to minimize it. The present invention advocates building the CCD with smaller cells and more of them, as stated earlier, and further building the CCD in such manner as to promote intercell coupling—which can be capacitive or conductive or both—so as to obtain controlled mixing of the contents of nearby cells. The specification of the leakage is as follows: Given the accumulation or exposure time T during which the detector cells are being stimulated by particles from the particle flux, the leakage rate (hence the values of the capacitive and conductive leakage parameters) should be such that if charge were placed on only one detector cell at time t=O, and if one were to plot how the charge is distributed among that cell and its neighbors at time t=T, one would obtain a curve that matches the cylindrical weighting function (i.e., the impulse response) of the bandlimiting filter that would have been chosen to operate on the output of the CCD for that particular application. While the cylindrical weighting function cannot usually be matched exactly, its general character will be similar just from the physics of the leakage process, and its width parameter—the FWHM—can be matched very closely.

For the version of the mixing process that operates at the input to the detector, the original particle flux can be made to impinge on a target ahead of the CCD, the target being so constructed that a hit by an original particle gives rise to a shower of secondary particles. An example is provided by a common method used in X-ray technology. X-ray photons are too energetic to be efficiently absorbed by the silver halide layer of photographic film. Thus in the X-ray art the exposure of film is promoted by placing in the path of the X-rays a so-called intensifying screen, a layer of luminescent crystals (most often, calcium tungstate) deposited on a thin support, and placed in close contact with the film. Each X-ray photon hitting the crystal produces a shower of light photons, and the latter expose the film. In X-ray practice, the intensifying screen is installed as close to the film as possible, to prevent divergence of the shower of light photons from reducing system resolution. Here, however, the object if to perform the bandlimiting of the present invention. One first builds a CCD or other array of discrete detectors with very small cells and more of them, and then mounts a screen so spaced from the detector plane that the shower of light photons spreads to cover a number of nearby cells. The spacing is fixed so that, if one were to plot the numbers of light photons per unit area striking the cells of the detector plane, the plot would match the impulse response of the bandlimiting filter one would have chosen, according to this invention, for that particular application. It is clear that the general character of the plot will match the required impulse response, since both functions will be cylindrically-symmetric, non-negative, monotonically non-increasing; thus, even if the two plots don't match in detail, if the spacing between screen and detector plane is fixed so that the FWHM's of the plots are equal, the system will produce a good approximation to the band-limited output of the detector.

If the consumer of the images is a computer, then the computer will often be processing much more slowly than thirty images per second. The computer itself, or an associated processor, can perform the FFT's required to low-pass the oversampled signal. In extremely low-photon applications, the EXSTASE statistical estimation may be required to produce acceptable images.

The invention can be used with nearly-standard cameras made with standard CCD chips as follows. Suppose that a standard CCD chip has an array of R rows and C columns of image plane pixels. A camera using the invention could increase the number of pixels in one dimension only, for instance doubling or quadrupling the number of columns C while R stays constant. As the R×2C or R×4C CCD array is read out line-by-line, an ordinary lumped-constant low-pass filter attached to the output of the CCD will produce the desired band-limited signal, which can then be resampled with C samples per horizontal line. This method is useful because it is computationally less demanding. This oversampling camera can be built using standard CCD chips and cylindrical optics having different magnification in the row and column dimensions to project the object being viewed onto the array of CCD chips.

The low-pass filtering of the invention is ideally of the same dimensionality as the data itself: for instance, to process two-dimensional image data, it is desirable to use a two-dimensional filter. However, multiple one-dimensional filters can be combined to achieve much of the benefit of the invention without the computational demand of two-dimensional filtering. For instance, the R×C image plane of a CCD camera can be replaced with one that oversamples by a factor f in both dimensions. This CCD would be read out in columns and low-pass filtered in a one-dimensional filter. The filtered columns would be reassembled, then read out in rows, and each row low-pass filtered in a one-dimensional filter. This technique would be facilitated by a CCD chip that can be read along columns (rather than the conventional rows), and a fast shift register that can be loaded column-by-column with the output of the first filter, and then read out row-by-row to provide input to the second filter. Such shift registers are within the current state of the art as described, for example, in IEEE Spectrum, May 1992, p. 30 et seq.

What is claimed is:

1. A method for forming a representation of a flux of discrete particles emitted by a plurality of particle emitters, particle emission by each said particle emitter being a random process substantially unaffected by particle emission by any other of said particle emitters, the random process imparting a random noise variation to the particle flux, the particle flux having an information-carrying variation having a bandwidth of interest, the method comprising the steps of:

detecting particles of the particle flux, and for each detected particle producing a quantized representation datum of said detection, said quantized representation being determined by a quantization cell size that is smaller than a contrast cell size sufficiently small to preserve contrast for the smallest feature of interest of said information-carrying variation of the particle flux; and filtering said quantized representation data through a band-limiting filter of bandwidth less than a bandwidth corresponding to said quantization cell size but greater than said bandwidth of interest.

2. A method for forming a representation of a flux of discrete particles emitted by a plurality of particle emitters, the particle flux having an information-carrying variation having a bandwidth of interest and a random noise variation, said noise variation being such that particle flux values measured by any two non-overlapping particle detectors of any cell size will be statistically independent, and an aggregate variance of fluctuations of the particle flux being non-increasing as a particle detector of fixed total detection area is subdivided into smaller cells, the method comprising the steps of:

detecting particles of the particle flux, and for each detected particle producing a quantized representation datum of said detection, said quantized representation being determined by a quantization cell size that is smaller than a contrast cell size sufficiently small to preserve contrast for the smallest feature of interest of said information-carrying variation of the particle flux; and filtering said quantized representation data through a band-limiting filter of bandwidth less than a bandwidth corresponding to said quantization cell size but greater than said bandwidth of interest.

3. A method for forming a representation of a flux of discrete particles emitted by a plurality of independent particle emitters, particle arrival at a cell of a detector of the particles being a Poisson process, the particle flux having an information-carrying variation having a bandwidth of interest, the method comprising the steps of:

detecting particles of the particle flux, and for each detected particle producing a quantized representation datum of said detection, said quantized representation being determined by a quantization cell size that is smaller than a contrast cell size sufficiently small to preserve contrast for the smallest feature of interest of said information-carrying variation of the particle flux; and filtering said quantized representation data through a band-limiting filter of bandwidth less than a bandwidth corresponding to said quantization cell size but greater than said bandwidth of interest.

4. The method of any one of claims 1, 2, or 3, further comprising the step of flattening outliers of said data before said filtering step.

5. The method of claim 4 in which the said outlier flattening step comprises the steps of comparing the difference that is measured between, on the one hand, the values in a first neighborhood which includes a cell of interest, and on the other hand, the values in a second neighborhood which at least partially surrounds the said first neighborhood, with an upper bound, and if the said difference exceeds the said upper bound, replacing the values in the cell of interest with new values that satisfy the said upper bound.

6. The method of any one of claims 1, 2, or 3, further comprising the step of:

choosing said quantization cell size to be sufficiently small that essentially all of the quantization cells each detect at most one particle of the particle flux.

7. The method of any one of claims 1, 2, or 3, wherein:

said band-limiting filter has a substantially non-negative and non-oscillatory response; and said filtered representation data approximate a continuous particle flux density function over the area of said particle detector, an integral of said particle flux density function over any set of cells of said quantized representation being approximately equal to the total number of particles detected in the cells of said set.

8. The method of claim 7 further comprising the step of:

using said particle flux density function to form a visible image.

9. The method of any one of claims 1, 2, or 3, further comprising the step of:

using said filtered representation data to approximate an ensemble average of the particle flux.

10. The method of any one of claims 1, 2, or 3 further comprising the step of:

performing said filtering using a cylindrically-symmetric filter.

11. The method of any one of claims 1, 2, or 3, further comprising the step of:

before displaying said filtered representation data or data derived from said filtered representation data as a visible image, adding random numbers to at least a portion of said data, a standard deviation of the random number added to each datum being related to an uncertainty in the value of the datum.

12. The method of any one of claims 1, 2, or 3, wherein:

the particles are photons, said detection is performed by a two-dimensional photon detector, and said quantized representation data each include two spatial dimensions.

13. The method of claim 12 wherein:

said two-dimensional photon detector is a charge-coupled device array.

14. The method of claim 12 wherein:

said photon detector is a continuous device, not intrinsically subdivided into discrete detection cells;

the method further comprising the steps of:

quantizing locations of particles detected by said continuous detector into quantization cells; and recording said quantized detection locations in a memory of a computer.

15. The method of claim 12 further comprising the steps of:

configuring said photon detector to evaluate an energy of each said detected photon; and recording photon detections at energies in an energy window lying above a peak of said photon energies.

16. The method of claim 12 further comprising the steps of:

configuring said photon detector to evaluate an energy of each said detected photon, the energies of the particles being clustered in at least two peaks, photons in a lower-energy of said peaks being more abundant than photons in a higher-energy of said peaks; and recording photon detections at energies in an energy window corresponding to said higher-energy peak.

17. The method of claim 16 further comprising the step of:

recording photon detections at energies in an energy window lying above said higher-energy peak.

18. The method of any one of claims 1, 2, or 3, further comprising the step of:

resampling said filtered data at a sampling rate greater than a rate corresponding to said filter bandwidth.

19. The method of any one of claims 1, 2, or 3, wherein said producing of said quantized representation data comprises the steps of:

detecting the particles in a detector with a relatively large quantization cell size;

defining an array of cells, each cell of said detector corresponding to a contiguous group of cells of said array; and randomly redistributing particle detections from each of said large cells among corresponding cells of said array.

20. The method of claim 19, the redistributing step further comprising the step of:

assigning redistribution probabilities to each of said array cells, said redistribution probabilities corresponding to a smooth curve fit to data counts in each of said large cells.

21. The method of any of claims 1, 2, or 3, wherein said band-limiting filter is the beam of a display monitor, said beam having a cross section shape approximating the impulse response of a band-limiting filter.

22. The method of any of claims 1, 2, or 3, wherein said band-limiting filter comprises capacitance and/or conductance providing leakage coupling between cells of a detector of said particles.

23. The method of any of claims 1, 2, or 3, wherein said band-limiting filter is a target interposed between said particle emitters and a detector of said particles, the target configured to intercept each said particle and in response produce a shower of secondary particles for detection by said particle detector, each said shower having a cross section at the plane of said particle detector corresponding to the cross section of the impulse response of a desired band-limiting filter.

24. The method of any of claims 1, 2, or 3, wherein each of said quantized representation data has a first value and a quantized location, the method further comprising the steps:

at each datum, evaluating values of data at neighboring locations to differentiate stationary regions and edge regions of said data, said stationary regions being regions of said data in which the first values of neighboring data are relatively similar, said edge regions being regions of said data in which the first values of neighboring data are relatively dissimilar;

for data within said stationary regions, determining an estimated value for each said quantized location as a weighted average of said first values over a relatively large neighborhood of data neighboring a said quantized location in said stationary region; and for data within said edge regions, determining an estimated value for each said quantized location as a weighted average of said first values over a relatively small neighborhood of data neighboring a said quantized location in said edge region.

25. The method of any of claims 1, 2, or 3, wherein each of said quantized representation data has a first value and a quantized location, the method further comprising the step:

for quantized vector locations within said edge regions and lying near one of said stationary regions, determining an estimated value by extrapolating from values of data in said near stationary region.

26. The method of any one of claims 1, 2, or 3, further comprising the step of:

choosing each dimension of said quantization cell size to be at most half the corresponding dimension of a detector cell size corresponding to Nyquist sampling of said bandwidth of interest in said dimension.

27. A method of processing a numerical image of data acquired by a location-quantizing detector, the data each having a first value and a quantized location, comprising the steps:

at each datum, evaluating values of data at neighboring locations to differentiate stationary regions and edge regions of said data, said stationary regions being regions of said data in which the first values of neighboring data are relatively similar, said edge regions being regions of said data in which the first values of neighboring data are relatively dissimilar;

for data within said stationary regions, determining an estimated value for each said quantized location as a weighted average of said first values over a relatively large neighborhood of data neighboring a said quantized location in said stationary region; and for data within said edge regions, determining an estimated value for each said quantized location as a weighted average of said first values over a relatively small neighborhood of data neighboring a said quantized location in said edge region.

28. A method of processing a numerical image of data acquired by a location-quantizing detector, the data each having a first value and a quantized location, comprising the steps of:

at each datum, evaluating values of data at neighboring locations to differentiate stationary regions and edge regions of said data, said stationary regions being regions of said data in which the first values of neighboring data are relatively similar, said edge regions being regions of said data in which the first values of neighboring data are relatively dissimilar; and for quantized vector locations within said edge regions and lying near one of said stationary regions, determining an estimated value by extrapolating from values of data in said near stationary region.

29. The method of either of claims 27 or 28, wherein the step of differentiating said stationary regions and edge regions comprises the steps of:

determining the variability of values of said first data in a neighborhood around each datum;

comparing said neighborhood variabilities to a first threshold value;

for a second neighborhood around each pixel, counting the number of neighborhoods within said second neighborhood whose neighborhood variabilities exceed said threshold;

if said neighborhood count exceeds a second threshold, assigning the datum to a stationary region; and if said neighborhood count is less than a third threshold, assigning the datum to an edge region.

30. The method of either of claims 27 or 28, wherein said relatively low and relatively high variability conditions are determined at each datum by the steps of:

determining the ratio of the mean of said first values in said neighborhood to a variance of said first values in said neighborhood; and comparing said ratio to a threshold value.

31. The method of either of claims 27 or 28, further comprising the step of:

flattening outliers of said data before said evaluating and differentiating step.

32. The method of either of claims 27 or 28, wherein:

the evaluating and differentiating step further comprises the step of producing a state map array of entries corresponding to the data of said image, each entry of said map indicating whether the corresponding image datum is in a stationary region or an edge region.

33. The method of claim 27 further comprising the step of:

for quantized locations within said edge regions and lying near one of said stationary regions, determining an estimated value by extrapolating from values of data in said near stationary region.

34. The method of either of claims 33 or 28, wherein:

for quantized vector locations within said edge regions and lying near two or more of said stationary regions, determining an estimated value by choosing a preferred one of said near stationary regions, and extrapolating from values of data in said preferred stationary region.

35. A method of producing a perceptible image on a display device, the display device configured to display pixels of said image, each pixel corresponding to a region of an object to be imaged and having a color value, the method comprising the steps of:

acquiring average and uncertainty color values corresponding to each pixel of a portion of the image, said average value estimating a value of a property in said corresponding region and said uncertainty value corresponding to an uncertainty in said average value; and adding a random number to the average value for each pixel of said image portion, a standard deviation of each random number being related to said uncertainty value for the pixel; and displaying said randomized pixel values on the display device.

36. The method of claim 35 further comprising the steps of:

acquiring raw data from a transducer that samples a physical phenomenon; and performing a noise-reducing image processing step on said raw data to produce said average and uncertainty values before said adding step.

37. The method of claim 35 further comprising the step of:

selecting said image portion by randomly selecting a proportion of the pixels of said image.

38. The method of claim 35 further comprising the step of:

selecting said image portion by deterministically selecting a uniformly-distributed set of the pixels of said image.

39. A method for improving the images produced by a device for forming an image of detected particles of a particle flux, the particle flux having an information-carrying variation having a bandwidth of interest and a random noise variation, the device having a particle detector that, for each detected particle, produces a quantized representation datum of said detection, the method comprising the steps of:

replacing the particle detector with a particle detector having a quantization cell size that is smaller than a contrast cell size sufficiently small to preserve contrast for the smallest feature of interest of said information-carrying variation of the particle flux, for sampling said information-carrying variation of the particle flux; and adding to the image device a filter for band-limiting said quantized representation data, said filter having a bandwidth less than a bandwidth corresponding to said quantization cell size but greater than said bandwidth of interest.

40. A method for forming a continuous representation of a discrete process, comprising the steps of:

detecting events of said discrete process with a detector cell size sufficiently small that almost all cells of said detector count at most one said event;

constructing from said detected events a count density function;

estimating from said count density function an ensemble average count density function.

41. A method for reducing aliasing noise from sampled data, comprising the steps of:

sampling a phenomenon in a detector with a relatively large quantization cell size to produce a value for each cell of said detector;

defining an array of cells, each said detector cell corresponding to a contiguous group of cells of said defined array; and randomly partitioning the value of each said detector cell among corresponding cells of said defined array.

42. The method of claim 41, the redistributing step further comprising the step of:

assigning redistribution probabilities to each of said array cells, said redistribution probabilities corresponding to a smooth curve fit to data counts in each of said large cells.

43. Apparatus for forming a representation of a flux of discrete particles emitted by a plurality of particle emitters, particle emission by each said particle emitter being random and substantially unaffected by particle emission by any other of said particle emitters and thus imposing a random noise variation on the particle flux, the particle flux having an information-carrying variation having a bandwidth of interest, the apparatus comprising:

a particle detector for detecting particles of the particle flux, and for each detected particle producing a quantized representation datum of said detection, said particle detector having a quantization cell size that is smaller than a contrast cell size sufficiently small to preserve contrast for the smallest feature of interest of said information-carrying variation of the particle flux; and a band-limiting filter for filtering said quantized representation data, said filter having a bandwidth less than a bandwidth corresponding to said quantization cell size but greater than said bandwidth of interest.

44. A method for deconvolution filtering for processing a numerical image of data acquired by a location-quantizing detector, the data each having a first value and a quantized location, comprising the steps:

at each datum, evaluating said first values of data at neighboring locations to differentiate stationary regions and edge regions of said data, said stationary regions being regions of said data in which the first values of neighboring data are relatively similar, said edge regions being regions of said data in which the first values of neighboring data are relatively dissimilar;

for each datum not near a boundary between said stationary regions and said edge regions, filtering using an integration area centered on said datum and with a radius not exceeding a distance to said boundary; and for each datum near a stationary edge/boundary, filtering using an integration area asymmetric about said datum.

45. A method for forming a representation of a flux of discrete particles emitted by a plurality of particle emitters, particle emission by each said particle emitter being random and substantially unaffected by particle emission by any other of said particle emitters, thereby imparting a random variation to the particle flux, the particle flux having an information-carrying variation having a bandwidth of interest, said method comprising the steps of:

oversampling the particle flux for producing a quantized representation of the particle flux;

filtering said oversampled representation through a band-limiting filter for substantially removing all of said random noise variation energy outside said bandwidth of interest; and storing said filtered signal for further image processing or display.

* * * * *

UNITED STATES PATENT AND TRADEMARK OFFICE
CERTIFICATE OF CORRECTION

PATENT NO. : 5,489,782
DATED : February 6, 1996
INVENTOR(S) : Robert E. Wernikoff It is certified that error appears in the above-indentified patent and that said Letters Patent is hereby corrected as shown below:

Col. 6, line 4, replace "bandlimited" with --band-limited--.

Col. 13, line 62, replace "grey" with --gray--.

Col. 17, line 46, replace "alone" with --along--.

Col. 21, line 51, after "marker" insert --.--.

Col. 22, line 64, replace "at" with --of--.

UNITED STATES PATENT AND TRADEMARK OFFICE
CERTIFICATE OF CORRECTION

PATENT NO. : 5,489,782

DATED : February 6, 1996

INVENTOR(S) : Robert E. Wernikoff

It is certified that error appears in the above-indentified patent and that said Letters Patent is hereby corrected as shown below:

Col. 24, line 20, replace "688" with --668--.

Col. 28, line 23, replace "EXTASE" with --EXSTASE--.

Col. 29, line 6, after "misleadingly" insert --,--.

Col. 32, lines 24-25, move "in the special case of images, called projections, used" to line 26 after "in".

Col. 40, claim 44, line 47, replace "stationary edge/boundary" with --stationary/edge boundary--.

Signed and Sealed this

Twenty-ninth Day of April, 1997

BRUCE LEHMAN

Commissioner of Patents and Trademarks

Attest:

Attesting Officer